(12) United States Patent
O'Neill et al.

(10) Patent No.: US 9,913,744 B2
(45) Date of Patent: Mar. 13, 2018

(54) GASTROINTESTINAL DEVICE

(71) Applicant: Lean Medical Technologies, INC., Ann Arbor, MI (US)

(72) Inventors: William Gerald O'Neill, Maple Grove, MN (US); Richard Merrell Chesbrough, Bloomfield Hills, MI (US); Naresh Thomas Gunaratnam, Ann Arbor, MI (US); Vishal J. Bhagat, Ann Arbor, MI (US); Christopher John Gostout, Rochester, MN (US)

(73) Assignee: LEAN MEDICAL TECHNOLOGIES, INC., Ann Arbor, MI (US)

( * ) Notice: Subject to any disclaimer, the term of this patent is extended or adjusted under 35 U.S.C. 154(b) by 265 days.

(21) Appl. No.: 14/700,846

(22) Filed: Apr. 30, 2015

(65) Prior Publication Data
US 2015/0313741 A1    Nov. 5, 2015

Related U.S. Application Data

(60) Provisional application No. 61/986,814, filed on Apr. 30, 2014.

(51) Int. Cl.
*A61B 19/00* (2006.01)
*A61F 5/00* (2006.01)
(Continued)

(52) U.S. Cl.
CPC .......... *A61F 5/0089* (2013.01); *A61F 5/0036* (2013.01); *A61F 5/0076* (2013.01);
(Continued)

(58) Field of Classification Search
CPC ............ A61F 2220/0025; A61F 5/0036; A61F 5/0089; A61F 2/89; A61F 5/0076;
(Continued)

(56) References Cited

U.S. PATENT DOCUMENTS 5,108,420 A   4/1992 Marks
5,725,552 A   3/1998 Kotula et al.
(Continued)

OTHER PUBLICATIONS

US 8,668,662, 03/2014, Levine et al. (withdrawn)
International Search Report dated Aug. 3, 2015 for PCT Appn. No. PCT/US2015/028509 filed Apr. 30, 2015, 3 pgs.

*Primary Examiner* — Leslie Deak
(74) *Attorney, Agent, or Firm* — Merchant & Gould P.C.

(57) ABSTRACT

A gastrointestinal device for reducing flow through a pyloric sphincter of a patient is disclosed. The device may include a stent including a plurality of strands forming first and second ends, the plurality of strands configured to form a proximal portion having a proximal diameter and a distal portion having a distal diameter. The proximal and distal diameters may be larger than a diameter of the pyloric sphincter and the proximal diameter may be larger than the distal diameter. The device may include a connector assembly including proximal and distal connectors, the plurality of strands being attached to the proximal and distal connectors at the first and second ends. The connector assembly may further include a middle portion extending between the proximal and distal connectors. The middle connector may extend within the plurality of strands, and may be unattached to the plurality of strands.

19 Claims, 10 Drawing Sheets

(51) Int. Cl.
    *A61F 2/88* (2006.01)
    *A61F 2/90* (2013.01)
    *A61F 2/89* (2013.01)

(52) U.S. Cl.
    CPC .............. *A61F 5/0079* (2013.01); *A61F 2/88* (2013.01); *A61F 2/89* (2013.01); *A61F 2/90* (2013.01); *A61F 2220/0025* (2013.01); *A61F 2250/0059* (2013.01)

(58) Field of Classification Search
    CPC .. A61F 5/0079; A61F 2/88; A61F 2/90; A61F 2250/0059
    See application file for complete search history.

(56) References Cited

U.S. PATENT DOCUMENTS

| | | |
|---|---|---|
| 5,820,584 A | 10/1998 | Crabb |
| 5,846,261 A | 12/1998 | Kotula et al. |
| 5,853,422 A * | 12/1998 | Huebsch ............ A61B 17/0057 606/157 |
| 5,944,738 A | 8/1999 | Amplatz et al. |
| 5,976,174 A | 11/1999 | Ruiz |
| 6,123,715 A | 9/2000 | Amplatz |
| 6,168,622 B1 | 1/2001 | Mazzocchi |
| 6,210,338 B1 | 4/2001 | Afremov et al. |
| 6,241,678 B1 | 6/2001 | Afremov et al. |
| 6,334,864 B1 | 1/2002 | Amplatz et al. |
| 6,368,339 B1 | 4/2002 | Amplatz |
| 6,402,772 B1 | 6/2002 | Ampltz et al. |
| 6,447,531 B1 | 9/2002 | Amplatz |
| 6,468,301 B1 | 10/2002 | Amplatz et al. |
| 6,468,303 B1 | 10/2002 | Amplatz et al. |
| 6,506,204 B2 | 1/2003 | Mazzocchi |
| 6,579,303 B2 | 6/2003 | Amplatz |
| 6,599,308 B2 | 7/2003 | Amplatz |
| 6,605,102 B1 | 8/2003 | Mazzocchi et al. |
| 6,638,257 B2 | 10/2003 | Amplatz |
| 6,682,546 B2 | 1/2004 | Amplatz |
| 6,712,835 B2 | 3/2004 | Mazzocchi et al. |
| 6,932,837 B2 | 8/2005 | Amplatz et al. |
| 6,949,103 B2 | 9/2005 | Mazzocchi et al. |
| 6,989,019 B2 | 1/2006 | Mazzocchi et al. |
| 6,994,095 B2 | 2/2006 | Burnett |
| 7,001,409 B2 | 2/2006 | Amplatz |
| 7,025,791 B2 | 4/2006 | Levine et al. |
| 7,033,375 B2 | 4/2006 | Mazzocchi et al. |
| 7,048,752 B2 | 5/2006 | Mazzocchi et al. |
| 7,111,627 B2 | 9/2006 | Stack et al. |
| 7,122,058 B2 | 10/2006 | Levine et al. |
| 7,195,608 B2 | 3/2007 | Burnett |
| 7,267,694 B2 | 9/2007 | Levine et al. |
| 7,311,690 B2 | 12/2007 | Burnett |
| 7,329,285 B2 | 2/2008 | Levine et al. |
| 7,347,868 B2 | 3/2008 | Burnett et al. |
| 7,347,875 B2 | 3/2008 | Levine et al. |
| 7,367,985 B2 | 5/2008 | Mazzocchi et al. |
| 7,367,986 B2 | 5/2008 | Mazzocchi et al. |
| 7,371,250 B2 | 5/2008 | Mazzocchi et al. |
| 7,404,820 B2 | 7/2008 | Mazzocchi et al. |
| 7,410,492 B2 | 8/2008 | Mazzocchi et al. |
| 7,442,200 B2 | 10/2008 | Mazzocchi et al. |
| 7,476,256 B2 | 1/2009 | Meade et al. |
| 7,556,635 B2 | 7/2009 | Mazzocchi et al. |
| 7,556,636 B2 | 7/2009 | Mazzocchi et al. |
| 7,566,338 B2 | 7/2009 | Mazzocchi et al. |
| 7,572,273 B2 | 8/2009 | Mazzocchi et al. |
| 7,578,379 B2 | 8/2009 | Gillmore et al. |
| 7,578,830 B2 | 8/2009 | Kusleika et al. |
| 7,608,114 B2 | 10/2009 | Levine et al. |
| 7,621,886 B2 | 11/2009 | Burnett |
| 7,648,015 B2 | 1/2010 | Gillmore et al. |
| 7,670,355 B2 | 3/2010 | Mazzocchi et al. |
| 7,670,356 B2 | 3/2010 | Mazzocchi et al. |
| 7,678,068 B2 | 3/2010 | Levine et al. |
| 7,678,130 B2 | 3/2010 | Mazzocchi et al. |
| 7,682,330 B2 | 3/2010 | Meade et al. |
| 7,686,815 B2 | 3/2010 | Mazzocchi et al. |
| 7,695,446 B2 | 4/2010 | Levine et al. |
| 7,758,535 B2 | 7/2010 | Levine et al. |
| 7,766,861 B2 | 8/2010 | Levine et al. |
| 7,766,973 B2 | 8/2010 | Levine et al. |
| 7,771,382 B2 | 8/2010 | Levine et al. |
| 7,815,589 B2 | 10/2010 | Meade et al. |
| 7,815,591 B2 | 10/2010 | Levine et al. |
| 7,819,836 B2 | 10/2010 | Levine et al. |
| 7,828,815 B2 | 11/2010 | Mazzocchi et al. |
| 7,828,816 B2 | 11/2010 | Mazzocchi et al. |
| 7,837,643 B2 | 11/2010 | Levine et al. |
| 7,909,790 B2 | 3/2011 | Burnett |
| 7,922,732 B2 | 4/2011 | Mazzocchi et al. |
| 7,935,073 B2 | 5/2011 | Levine et al. |
| 7,947,060 B2 | 5/2011 | Mazzocchi et al. |
| 7,976,488 B2 | 7/2011 | Levine et al. |
| 7,981,163 B2 | 7/2011 | Meade et al. |
| 8,034,061 B2 | 10/2011 | Amplatz et al. |
| 8,048,147 B2 | 11/2011 | Adams |
| 8,048,169 B2 | 11/2011 | Burnett et al. |
| 8,057,420 B2 | 11/2011 | Meade et al. |
| 8,070,824 B2 | 12/2011 | Burnett et al. |
| 8,096,966 B2 | 1/2012 | Levine et al. |
| 8,137,301 B2 | 3/2012 | Levine et al. |
| 8,162,871 B2 | 4/2012 | Levine et al. |
| 8,163,004 B2 | 4/2012 | Amplatz et al. |
| 8,211,186 B2 | 7/2012 | Belhe et al. |
| 8,303,669 B2 | 11/2012 | Meade et al. |
| 8,313,505 B2 | 11/2012 | Amplatz et al. |
| 8,361,138 B2 | 1/2013 | Adams |
| 8,372,158 B2 | 2/2013 | Levy et al. |
| 8,398,577 B2 | 3/2013 | Burnett |
| 8,398,670 B2 | 3/2013 | Amplatz et al. |
| 8,425,451 B2 | 4/2013 | Levine et al. |
| 8,434,393 B2 | 5/2013 | Adams |
| 8,454,633 B2 | 6/2013 | Amplatz et al. |
| 8,486,153 B2 | 7/2013 | Levine et al. |
| 8,491,649 B2 | 7/2013 | Mach |
| 8,511,214 B2 | 8/2013 | Gries |
| 8,517,973 B2 | 8/2013 | Burnett |
| 8,579,988 B2 | 11/2013 | Burnett et al. |
| 8,597,224 B2 | 12/2013 | Vargas |
| 8,603,186 B2 | 12/2013 | Binmoeller |
| 8,621,975 B2 | 1/2014 | Russo et al. |
| 8,628,583 B2 | 1/2014 | Meade et al. |
| 8,636,683 B2 | 1/2014 | Chin et al. |
| 8,651,007 B2 | 2/2014 | Adams |
| 8,657,885 B2 | 2/2014 | Burnett et al. |
| 8,663,338 B2 | 3/2014 | Burnett et al. |
| 8,691,271 B2 | 4/2014 | Burnett et al. |
| 8,758,389 B2 | 6/2014 | Glimsdale |
| 8,771,219 B2 | 7/2014 | Meade et al. |
| 8,795,301 B2 | 8/2014 | Burnett et al. |
| 8,801,647 B2 | 8/2014 | Melanson et al. |
| 8,821,529 B2 | 9/2014 | Kariniemi et al. |
| 8,821,584 B2 | 9/2014 | Burnett et al. |
| 8,834,405 B2 | 9/2014 | Meade et al. |
| 8,834,553 B2 | 9/2014 | Melanson et al. |
| 8,840,679 B2 | 9/2014 | Durgin |
| 8,870,806 B2 | 10/2014 | Levine et al. |
| 8,882,698 B2 | 11/2014 | Levine et al. |
| 8,888,797 B2 | 11/2014 | Burnett et al. |
| 8,919,389 B2 | 12/2014 | Gries |
| 8,920,358 B2 | 12/2014 | Levine et al. |
| 2002/0138095 A1 | 9/2002 | Mazzocchi et al. |
| 2002/0169474 A1 | 11/2002 | Kusleika et al. |
| 2004/0192582 A1 | 9/2004 | Burnett et al. |
| 2004/0220682 A1 | 11/2004 | Levine et al. |
| 2004/0249362 A1 | 12/2004 | Levine et al. |
| 2005/0055039 A1 | 3/2005 | Burnett et al. |
| 2005/0080431 A1 | 4/2005 | Levine et al. |
| 2005/0119690 A1 | 6/2005 | Mazzocchi et al. |
| 2005/0125020 A1 | 6/2005 | Meade et al. |
| 2005/0228434 A1 | 10/2005 | Amplatz et al. |
| 2006/0020278 A1 | 1/2006 | Burnett et al. |
| 2006/0173300 A1 | 8/2006 | Oslund et al. |

(56) References Cited

U.S. PATENT DOCUMENTS

| | | |
|---|---|---|
| 2006/0212042 A1 | 9/2006 | Lamport et al. |
| 2006/0247680 A1 | 11/2006 | Amplatz et al. |
| 2006/0253184 A1 | 11/2006 | Amplatz |
| 2007/0032879 A1 | 2/2007 | Levine et al. |
| 2007/0049801 A1 | 3/2007 | Lamport et al. |
| 2007/0118207 A1 | 5/2007 | Amplatz et al. |
| 2007/0135831 A1 | 6/2007 | Burnett |
| 2007/0168018 A1 | 7/2007 | Amplatz et al. |
| 2007/0168019 A1 | 7/2007 | Amplatz et al. |
| 2007/0178160 A1 | 8/2007 | Burnett |
| 2007/0250132 A1 | 10/2007 | Burnett |
| 2007/0265656 A1 | 11/2007 | Amplatz et al. |
| 2007/0265658 A1 | 11/2007 | Nelson et al. |
| 2008/0208135 A1 | 8/2008 | Annunziata |
| 2008/0208239 A1 | 8/2008 | Annunziata |
| 2008/0208357 A1 | 8/2008 | Melanson et al. |
| 2009/0012372 A1 | 1/2009 | Burnett et al. |
| 2009/0062841 A1 | 3/2009 | Amplatz et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0171386 A1 | 7/2009 | Amplatz et al. |
| 2009/0182355 A1 | 7/2009 | Levine et al. |
| 2009/0182357 A1 | 7/2009 | Burnett et al. |
| 2009/0182358 A1 | 7/2009 | Burnett et al. |
| 2009/0187200 A1 | 7/2009 | Burnett et al. |
| 2009/0187201 A1 | 7/2009 | Burnett et al. |
| 2009/0187214 A1 | 7/2009 | Amplatz et al. |
| 2009/0198210 A1 | 8/2009 | Burnett et al. |
| 2009/0209855 A1 | 8/2009 | Drilling et al. |
| 2009/0210048 A1 | 8/2009 | Amplatz et al. |
| 2009/0216262 A1 | 8/2009 | Burnett et al. |
| 2009/0259236 A2 | 10/2009 | Burnett et al. |
| 2010/0023046 A1 | 1/2010 | Heidner et al. |
| 2010/0023048 A1 | 1/2010 | Mach |
| 2010/0030321 A1 | 2/2010 | Mach |
| 2010/0049307 A1 | 2/2010 | Ren |
| 2010/0063578 A1 | 3/2010 | Ren et al. |
| 2010/0106235 A1 | 4/2010 | Kariniemi et al. |
| 2010/0121370 A1 | 5/2010 | Kariniemi |
| 2010/0211046 A1 | 8/2010 | Adams et al. |
| 2010/0228272 A1 | 9/2010 | Balbierz et al. |
| 2010/0298632 A1 | 11/2010 | Levine et al. |
| 2010/0305590 A1 | 12/2010 | Holmes et al. |
| 2011/0004228 A1 | 1/2011 | Priplata et al. |
| 2011/0004230 A1 | 1/2011 | Levine et al. |
| 2011/0208234 A1 | 8/2011 | Mazzocchi et al. |
| 2011/0245752 A1 | 10/2011 | Levine et al. |
| 2011/0257580 A1 | 10/2011 | Meade et al. |
| 2011/0276091 A1 | 11/2011 | Metanson et al. |
| 2012/0004676 A1 | 1/2012 | Vargas |
| 2012/0029413 A1 | 2/2012 | Meade et al. |
| 2012/0065571 A1 | 3/2012 | Thompson et al. |
| 2012/0095385 A1 | 4/2012 | Dominguez et al. |
| 2012/0095483 A1 | 4/2012 | Babkes et al. |
| 2012/0095494 A1 | 4/2012 | Dominguez et al. |
| 2012/0123556 A1 | 5/2012 | Durgin |
| 2012/0179086 A1 | 7/2012 | Shank et al. |
| 2012/0184893 A1 | 7/2012 | Thompson et al. |
| 2012/0197376 A1 | 8/2012 | Heidner et al. |
| 2012/0215152 A1 | 8/2012 | Levine et al. |
| 2012/0245623 A1 | 9/2012 | Kariniemi et al. |
| 2012/0245668 A1 | 9/2012 | Kariniemi et al. |
| 2012/0253259 A1 | 10/2012 | Belhe et al. |
| 2012/0253260 A1 | 10/2012 | Belhe et al. |
| 2012/0323267 A1 | 12/2012 | Ren |
| 2013/0012979 A1 | 1/2013 | Amplatz et al. |
| 2013/0030351 A1* | 1/2013 | Belhe .................. A61F 5/0076 604/9 |
| 2013/0073024 A1 | 3/2013 | Russo et al. |
| 2013/0079603 A1 | 3/2013 | Vargas |
| 2013/0131717 A1 | 5/2013 | Glimsdale |
| 2013/0204289 A1 | 8/2013 | Dsnurkar et al. |
| 2013/0218189 A1 | 8/2013 | Amplatz et al. |
| 2013/0253409 A1 | 9/2013 | Burnett |
| 2013/0253410 A1 | 9/2013 | Levine et al. |
| 2013/0304232 A1 | 11/2013 | Gries |
| 2013/0338565 A1 | 12/2013 | Burnett |
| 2013/0338566 A1 | 12/2013 | Burnett |
| 2014/0018719 A1 | 1/2014 | Chamorro, III et al. |
| 2014/0088635 A1 | 3/2014 | Russo et al. |
| 2014/0100512 A1 | 4/2014 | Meade et al. |
| 2014/0135827 A1 | 5/2014 | Amplatz et al. |
| 2014/0194805 A1 | 7/2014 | Levine et al. |
| 2014/0200502 A1 | 7/2014 | Belhe et al. |
| 2014/0214077 A1 | 7/2014 | Glimsdale |
| 2014/0249567 A1 | 9/2014 | Adams et al. |
| 2014/0257357 A1 | 9/2014 | Ren |
| 2014/0257360 A1 | 9/2014 | Keillor |
| 2014/0257361 A1 | 9/2014 | Prom |
| 2014/0257373 A1 | 9/2014 | Prom |
| 2014/0257374 A1 | 9/2014 | Heisel et al. |
| 2014/0277388 A1 | 9/2014 | Skemp |
| 2014/0277428 A1 | 9/2014 | Skemp et al. |
| 2014/0288591 A1 | 9/2014 | Amplatz et al. |
| 2014/0296768 A1 | 10/2014 | Meade et al. |
| 2014/0296770 A1 | 10/2014 | Holmes et al. |
| 2014/0303543 A1 | 10/2014 | Meade et al. |
| 2014/0358063 A1 | 12/2014 | Melanson et al. |
| 2015/0011969 A1 | 1/2015 | Burnett et al. |

\* cited by examiner

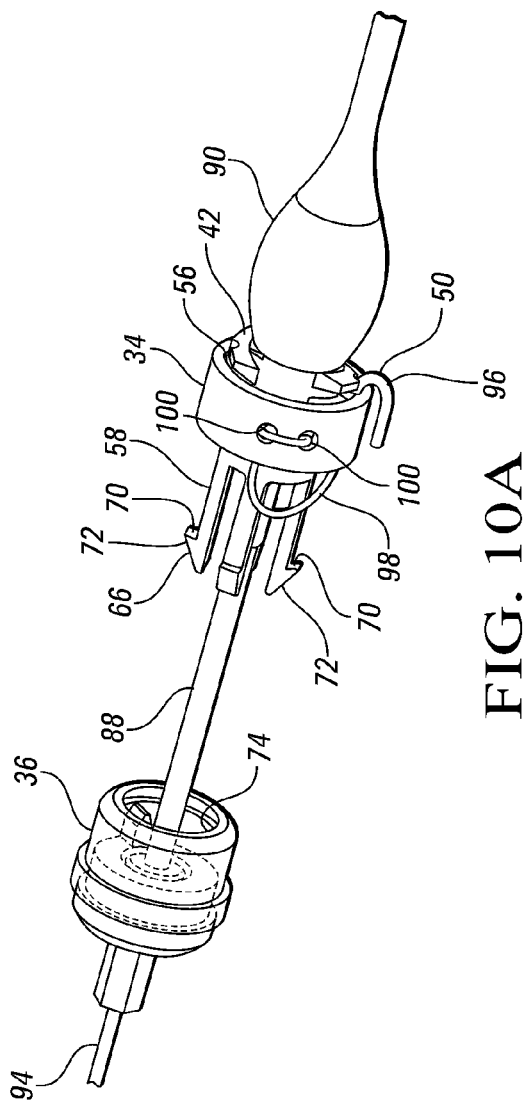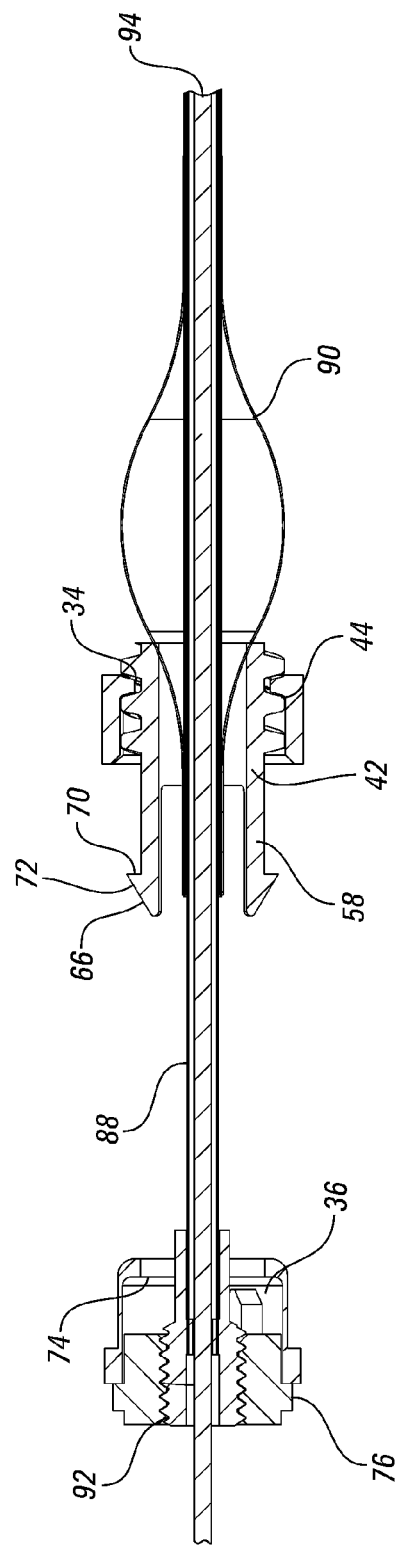

GASTROINTESTINAL DEVICE

CROSS-REFERENCE TO RELATED APPLICATIONS

This application claims the benefit of U.S. provisional application Ser. No. 61/986,814 filed Apr. 30, 2014, the disclosure of which is hereby incorporated in its entirety by reference herein.

TECHNICAL FIELD

The present disclosure relates to a gastrointestinal device, for example, to assist in weight loss.

BACKGROUND

Obesity (e.g., a body mass index (BMI) >30) is an epidemic in the United States and around the world, where an estimated greater than one-third of U.S. adults and over a billion people worldwide are obese. Obesity-related conditions, including heart disease, stroke, type 2 diabetes and certain types of cancer, are some of the leading causes of preventable death. The estimated annual medical cost of obesity in the U.S. was $147 billion in 2008 U.S. dollars; the medical costs for people who are obese were $1,429 higher than those of normal weight. Greater than 400,000 deaths in the United States each year are attributed to obesity.

Diet and exercise programs are effective in promoting weight loss, however, it is estimated that less than 5% of those who engage in such programs are able to sustain them long term. Surgical weight loss surgery is very effective, however, it is associated with morbidity and mortality rates between 0.1 and 2%. Weight loss surgery is typically reserved for the morbidly obese (e.g., a BMI >40), which accounts for less than 5% of the obese population. One example of an effective weight loss surgery is a Roux en Y gastric bypass, which is estimated to cost over $35,000 and includes up to three days of hospitalization.

SUMMARY

In at least one embodiment, a gastrointestinal device for reducing flow through a pyloric sphincter of a patient is provided. The device may include a stent including a plurality of strands forming first and second ends, the plurality of strands configured to form a proximal portion having a proximal diameter and a distal portion having a distal diameter. The proximal and distal diameters may be larger than a diameter of the pyloric sphincter and the proximal diameter may be larger than the distal diameter. The device may further include a connector assembly including a proximal connector and a distal connector. The plurality of strands may be attached at the first end to the proximal connector and at the second end to the distal connector.

In one embodiment, a ratio of the distal diameter to the proximal diameter is from 0.6:1 to 0.9:1. The proximal stent portion may be configured to prevent distal movement of the device through the pyloric sphincter and the distal stent portion may be configured to prevent proximal movement of the device through the pyloric sphincter. The connector assembly may define a lumen having a diameter that is less than the diameter of the pyloric sphincter and configured to reduce a flow of partially digested food through the pyloric sphincter. In one embodiment, the device further includes a sleeve fixed to the distal connector and configured to extend into a duodenum of the patient, the sleeve configured to receive partially digested food from the connector assembly.

The connector assembly may further comprise a middle portion extending between the proximal connector and the distal connector within the plurality of strands. The middle portion may include a threaded portion that is configured to engage a threaded portion of the proximal connector. The middle portion may include at least one projection extending towards the distal connector, the at least one projection including a snap fit element configured to engage a flange on the distal connector and prevent proximal movement of the middle portion relative to the distal connector.

The plurality of strands may extend in a proximal direction from the proximal portion to attach to the proximal connector at the first end and extend in a distal direction from the distal portion to attach to the distal connector at the second end. The first and second portions may be configured to straddle the pyloric sphincter and the first and second portions may each define proximal and distal opposing surfaces. The proximal diameter may taper to a reduced diameter adjacent to the proximal connector and the distal diameter may taper to a reduced diameter adjacent the distal connector. In one embodiment, the plurality of strands is embedded within an elastomer, such as silicone.

In at least one embodiment, a gastrointestinal device for reducing flow through a pyloric sphincter of a patient is provided. The device may include a stent including a plurality of strands forming first and second ends, the plurality of strands configured to form a proximal portion having a proximal diameter and a distal portion having a distal diameter. The proximal and distal diameters may be larger than a diameter of the pyloric sphincter. The device may further include a connector assembly including a proximal connector, a distal connector, and a middle portion extending therebetween. The plurality of strands may be attached at the first end to the proximal connector and at the second end to the distal connector, and the connector assembly middle portion may extend within the plurality of strands.

In one embodiment, a ratio of the distal diameter to the proximal diameter is from 0.6:1 to 0.9:1. The plurality of strands may be embedded within silicone. The middle portion may include a threaded portion that is configured to engage a threaded portion of the proximal connector and the middle portion may include at least one projection extending towards the distal connector. The at least one projection may include a snap fit element configured to engage a flange on the distal connector and prevent proximal movement of the middle portion relative to the distal connector.

In at least one embodiment, a gastrointestinal device for reducing flow through a pyloric sphincter of a patient is provided. The device may include a stent including a plurality of strands forming first and second ends, the plurality of strands configured to form a proximal portion having a proximal diameter and a distal portion having a distal diameter. The proximal and distal diameters may be larger than a diameter of the pyloric sphincter. The device may further include a connector assembly including a proximal connector, a distal connector, and a middle portion extending therebetween. The plurality of strands may be attached at the first end to the proximal connector and at the second end to the distal connector, and the connector assembly middle portion may be unattached to the plurality of strands.

In one embodiment, a ratio of the distal diameter to the proximal diameter is from 0.6:1 to 0.9:1. The middle portion may include a threaded portion that is configured to engage a threaded portion of the proximal connector and the middle portion may include at least one projection extending towards the distal connector. The at least one projection may include a snap fit element configured to engage a flange on the distal connector and prevent proximal movement of the middle portion relative to the distal connector.

BRIEF DESCRIPTION OF THE DRAWINGS

FIG. 10A is a perspective view of a connector assembly in an unlocked configuration, according to an embodiment;

FIG. 10B is a cross-section of the connector assembly of FIG. 10A.

DETAILED DESCRIPTION

Figure 1:
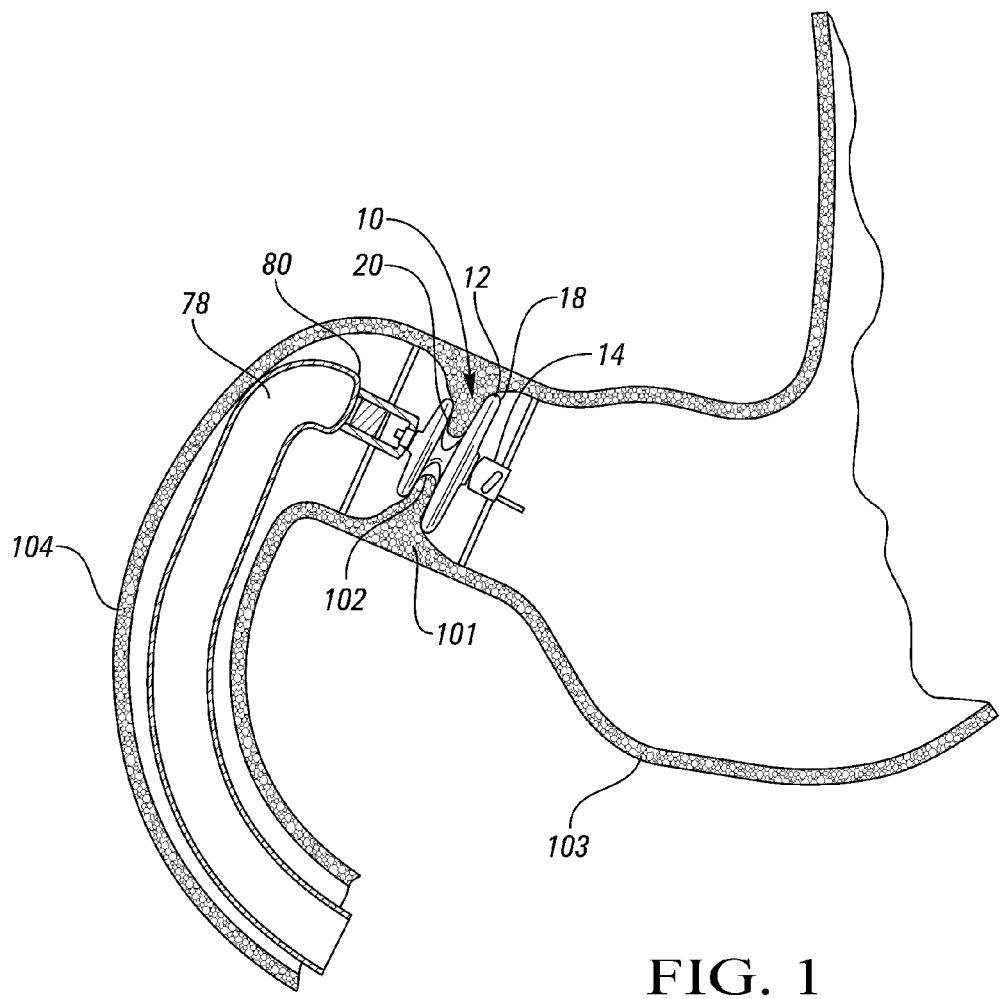
FIG. 1 is a schematic cut-away view of a deployed gastrointestinal device, according to an embodiment.
Figure 2:
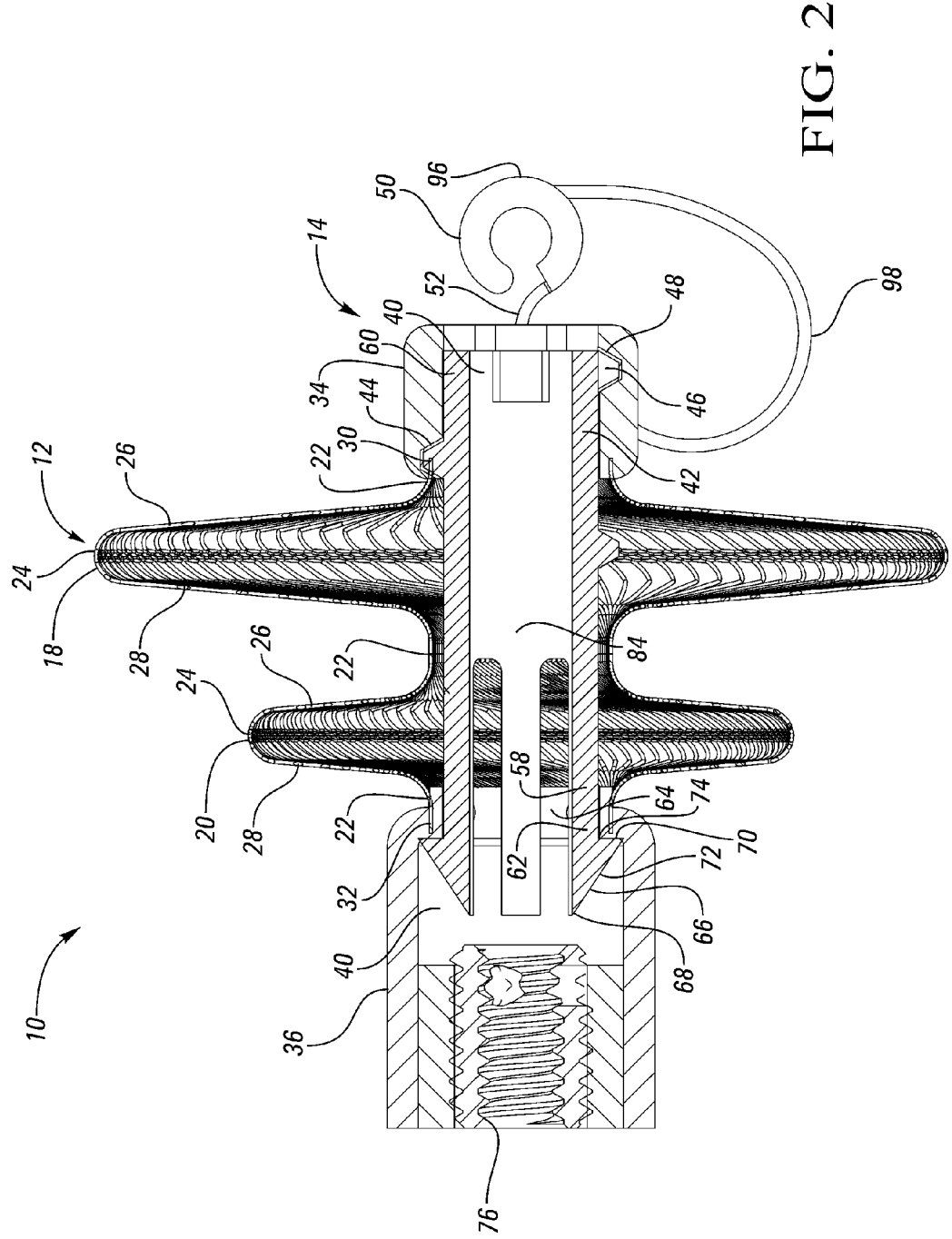
FIG. 2 is cross-section of a deployed gastrointestinal device, according to an embodiment.
Figure 3:
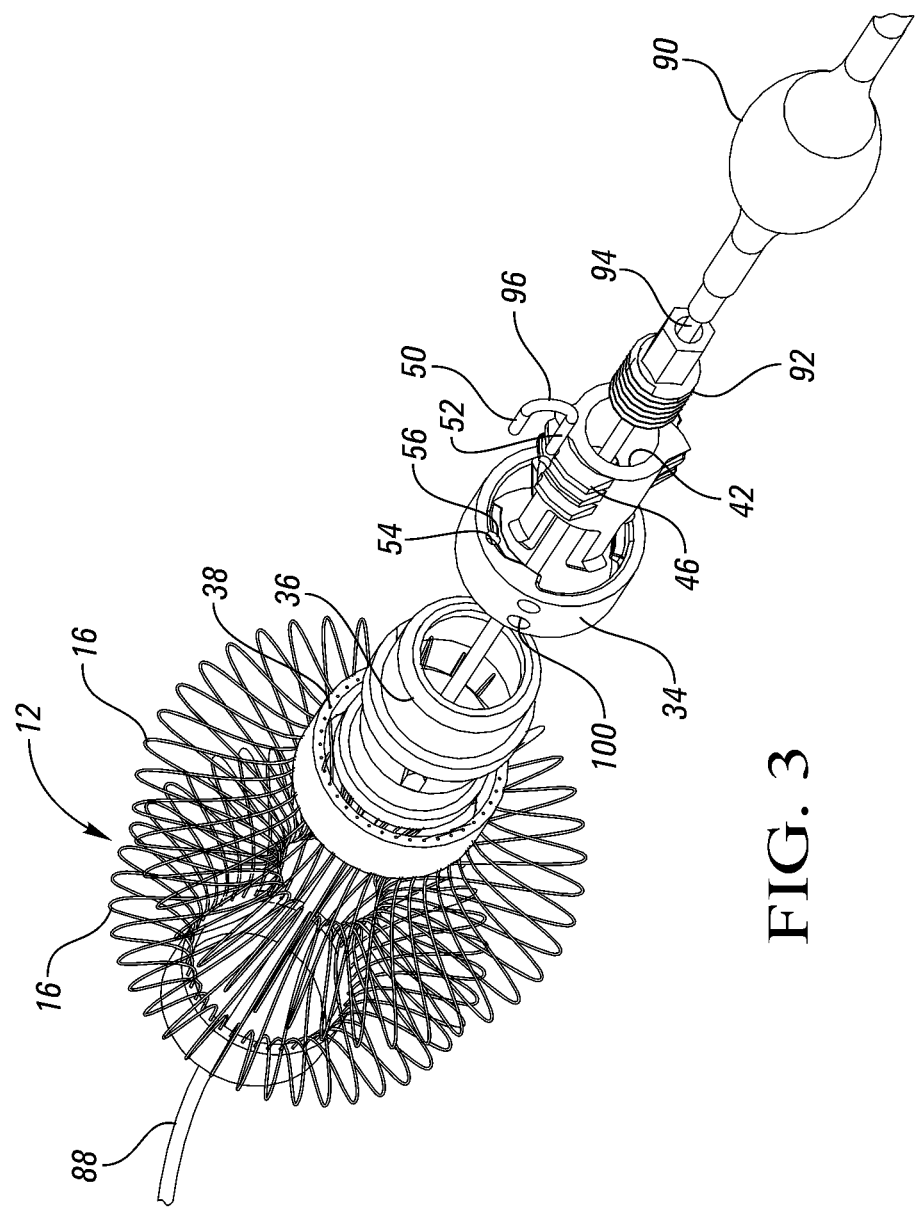
FIG. 3 is an exploded view of a gastrointestinal device, according to an embodiment.
Figure 4:
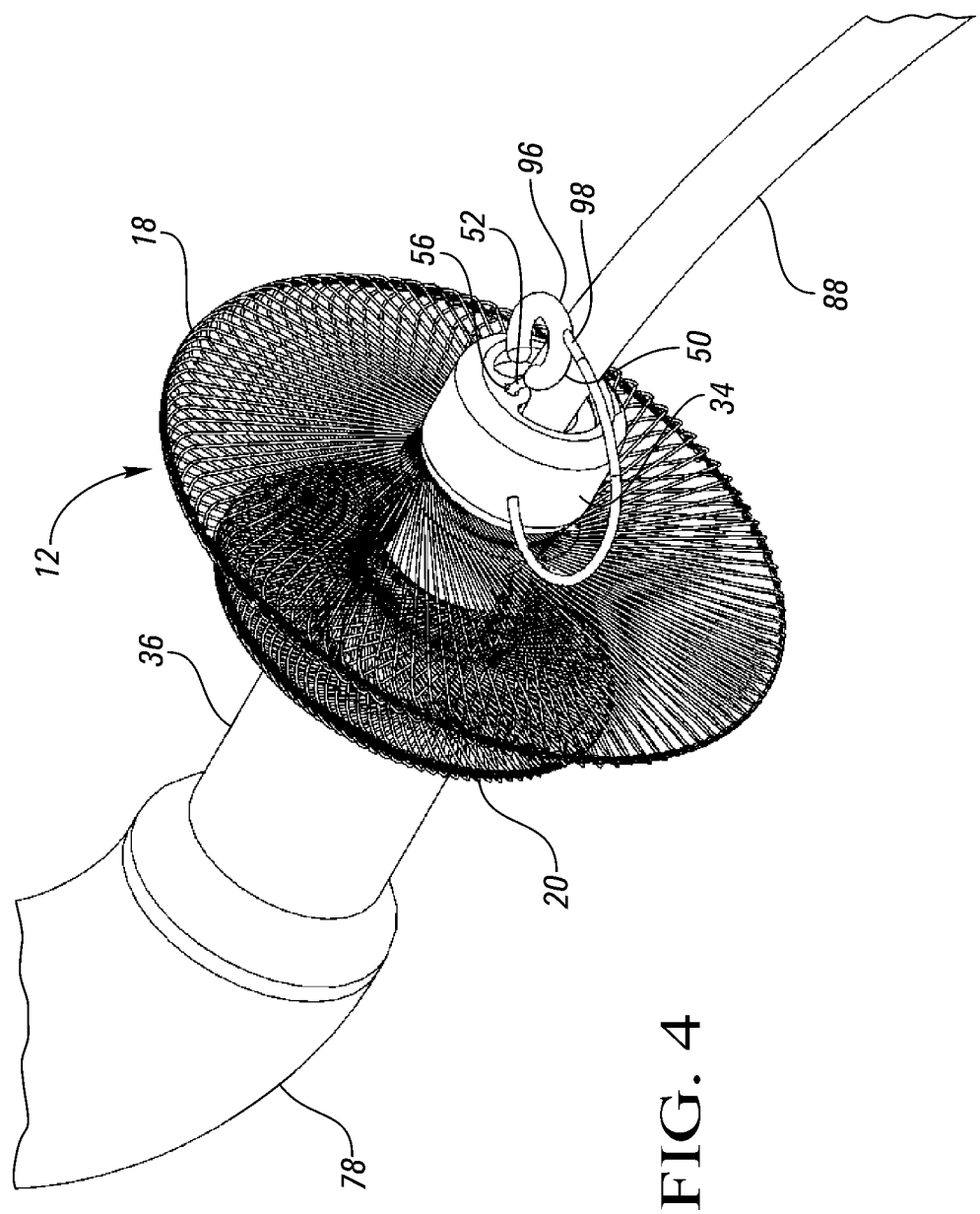
FIG. 4 is front perspective view of a deployed gastrointestinal device, according to an embodiment.
Figure 5:
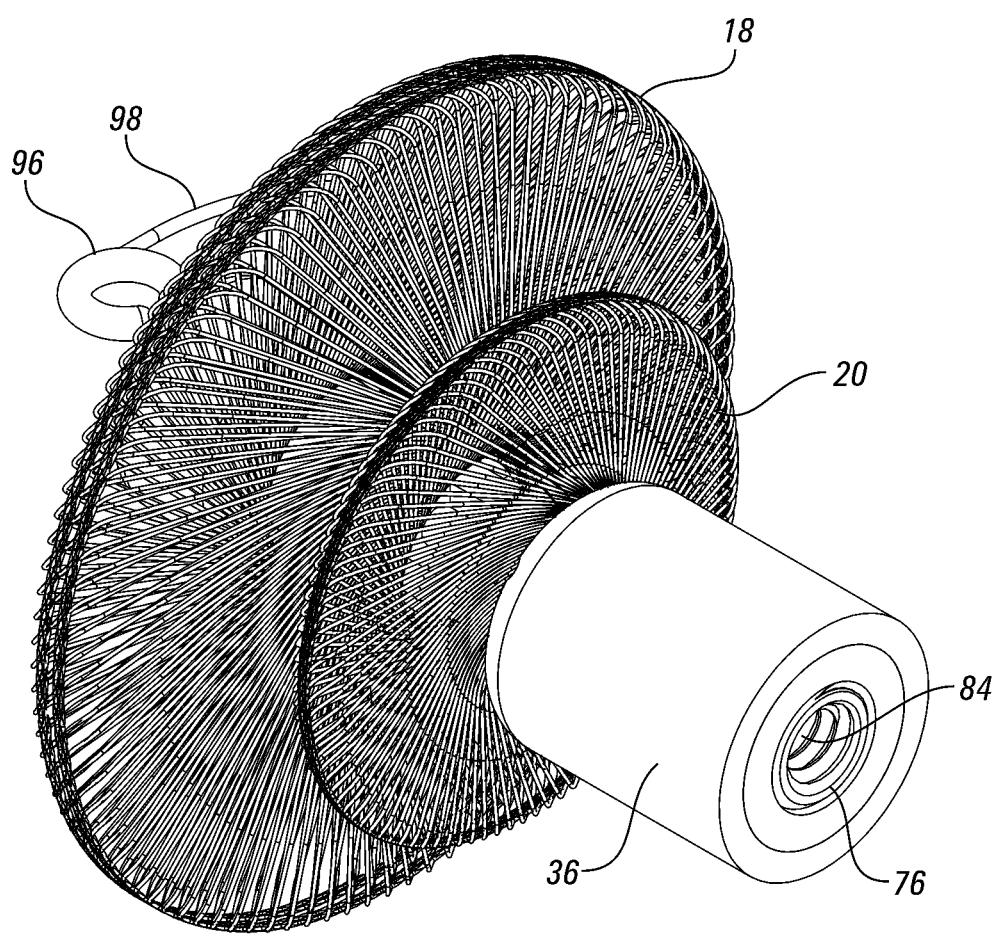
FIG. 5 is a rear perspective view of a deployed gastrointestinal device, according to an embodiment.
Figure 6A:
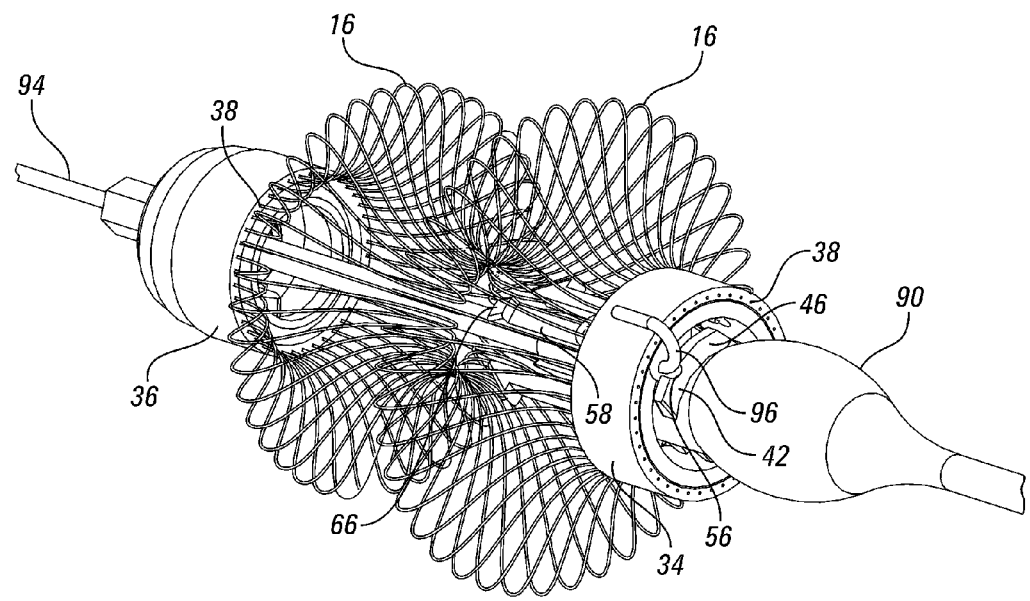
FIG. 6A is a perspective view of a gastrointestinal device in an unlocked configuration, according to an embodiment.
Figure 6B:
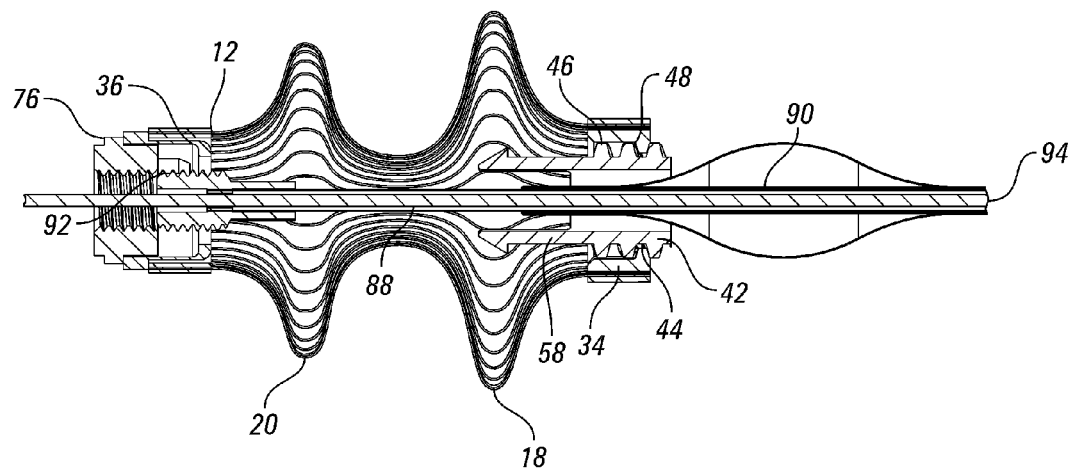
FIG. 6B is a cross-section of the device of FIG. 6A, according to an embodiment.
Figure 7:
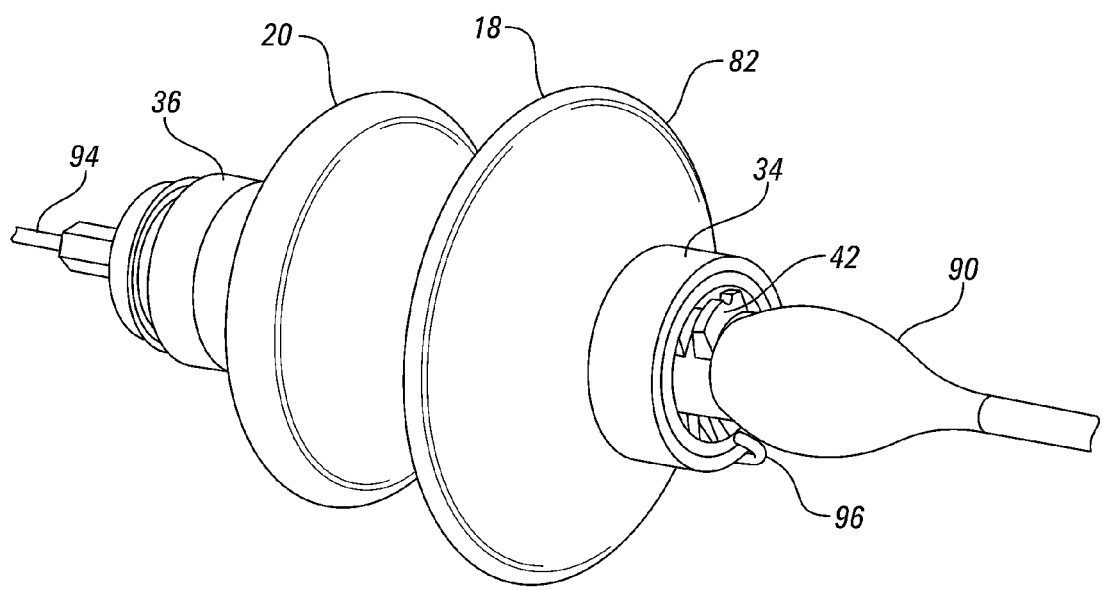
FIG. 7 is a perspective view of the device of FIG. 6A with a sleeve surrounding the stent, according to an embodiment.
Figure 8:
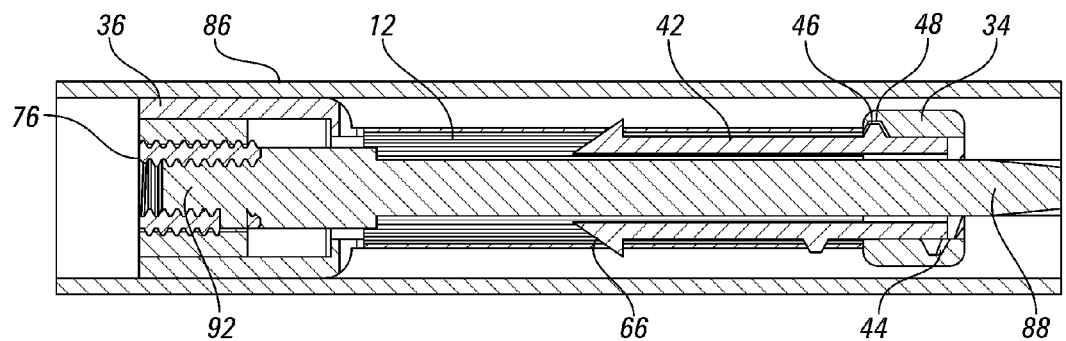
FIG. 8 is a cross-section of a gastrointestinal device in an insertion configuration, according to an embodiment.
Figure 9:
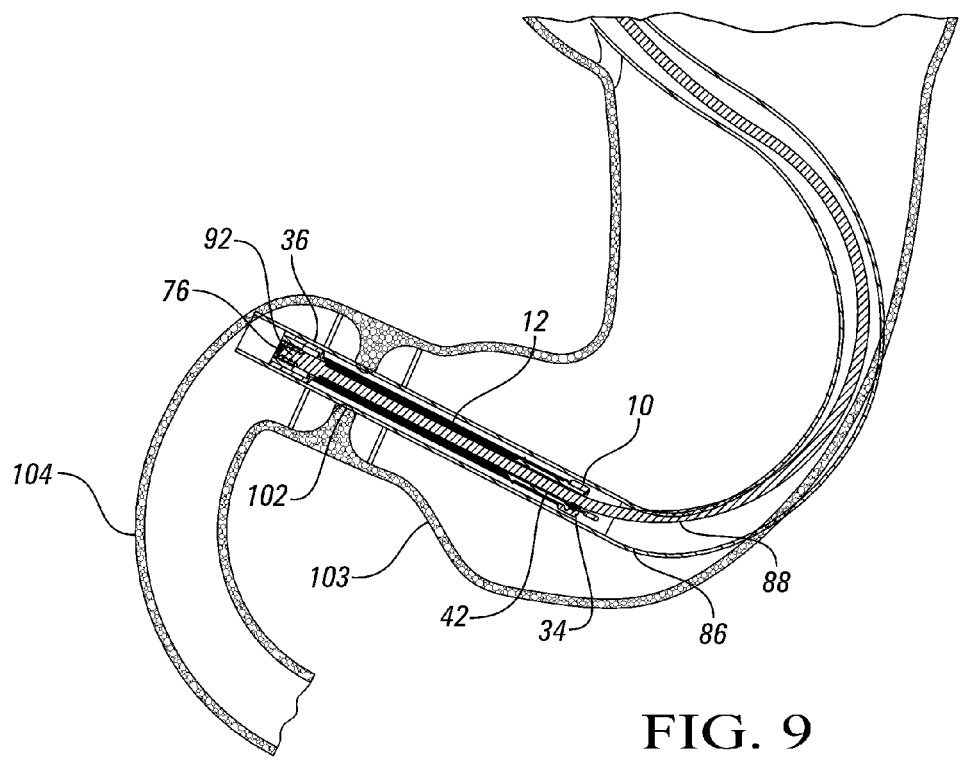
FIG. 9 is a schematic cut-away view of a gastrointestinal device in an insertion configuration, according to an embodiment.
Figure 11A:
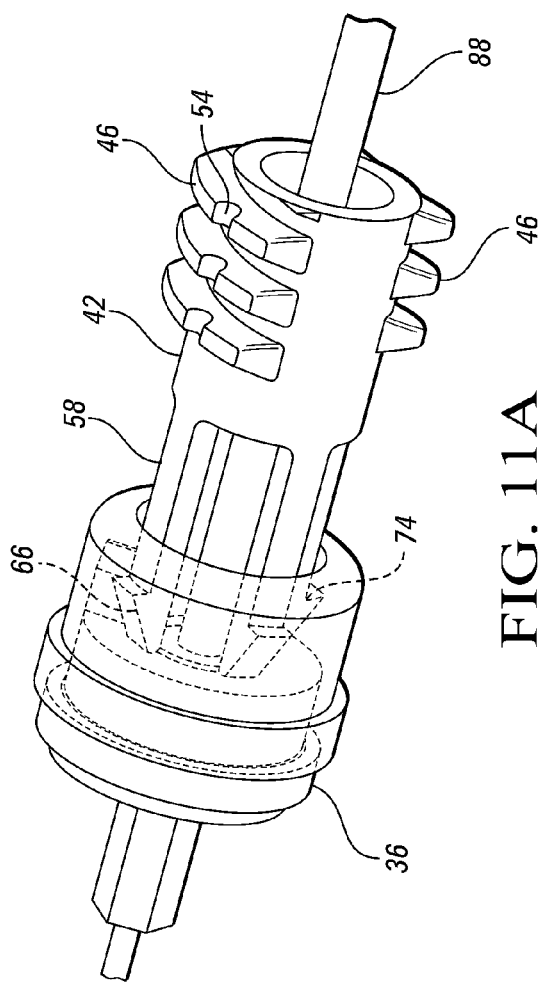
FIG. 11A is the connector assembly of FIG. 10 in a locked configuration.
Figure 11B:
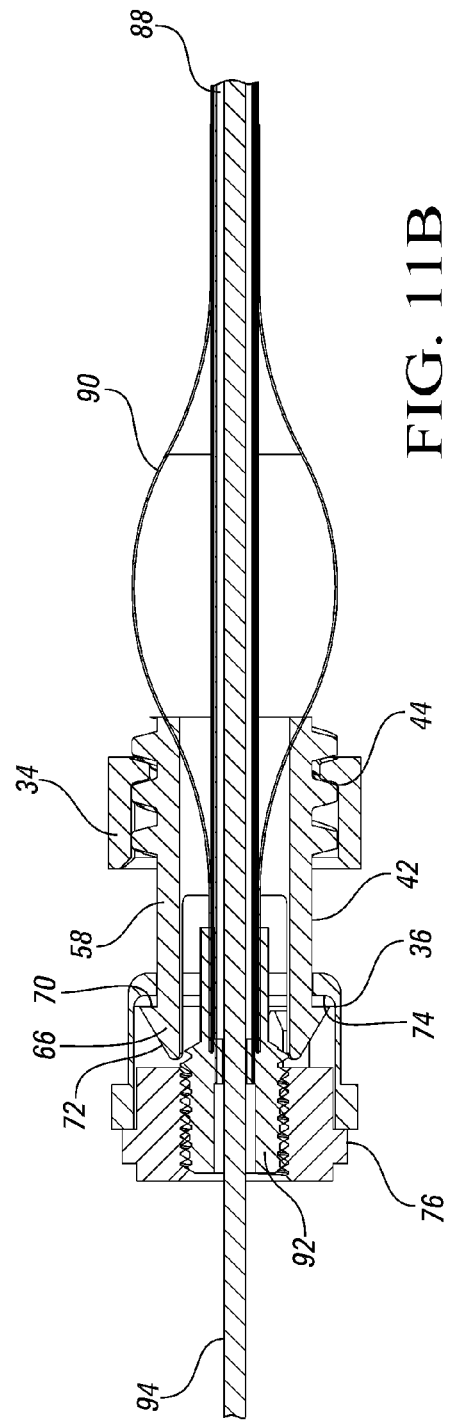
FIG. 11B is a cross-section of the connector assembly of FIG. 11A.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

As described in the Background, weight loss procedures are currently limited to surgical operations which may be costly, relatively risky, and may require extended hospitalization. In addition, surgery may permanently alter the bowel anatomy and can lead to permanent changes in bowel function including increased rates of abdominal pain and diarrhea. The Roux en Y gastric bypass is a highly invasive, permanent procedure. The procedure generally involves creating a 15-30 ml gastric pouch. The jejunum is divided and is anastomosed (connected) to the gastric pouch. A significant, but infrequent, early complication is a leak at the anastomotic or staple line. Leaks from the anastomosis have low frequency (0.4% to 5.2%) but have devastating consequences, with up to a 50% mortality rate. Postoperative hemorrhage is a more frequent event, cited in the literature as occurring between 1.9% to 4.4%. Small bowel obstruction is related to internal hernias and range from an incidence of 1% to 9%. Finally, a late complication may arise form Gastrojejunostamy anastomic stricture with incidence rates reported from 2.9% to 23% and appears to be more prevalent with laparoscopic procedures rather than open surgery. These relatively high rates of complications are directly related to the invasiveness of the surgery.

A byproduct of gastric bypass surgery is a significant reduction in type 2 diabetes. A team of researchers at Group Health Research Institute studied 4,434 diabetic patients for fourteen years from 1995 to 2008. All patients were obese enough to be candidates for bypass surgery. Two thirds of the study's patients had remission of diabetes after gastric surgery. However one third re-developed diabetes within five years of gastric surgery. The study suggests that after gastric surgery, diabetes may stay away longer in those people whose diabetes was less severe and at an earlier stage at the time of surgery.

Several devices are in development that attempt to provide non-surgical weight-loss alternatives. One device tries to mimic the Roux en Y bypass by placing a "sleeve" of PTFE through the duodenum and proximal jejunum to prevent absorption of gastric contents. In preliminary trials, the device appears to be effective in promoting weight loss and improving glycemic control in morbidly obese diabetics. Pilot studies showed the device improved serum glucose concentrations and HbA1c levels and reduced body weight.

However, there are some significant complications related to removal of the duodenal sleeve device. Complications may include device migration, device obstructions, abdominal pain, ulceration, perforation, and heptic abscesses. Fifteen of thirty nine implanted devices (38%) were removed before the end of one study. A similar percentage were removed in another study primarily due to migration, GI bleeding, and abdominal pain. The device is anchored to the first portion of the small bowel (the duodenal bulb) using metal barbs. Anchoring to this portion of the bowel increases the risk of dislodgement where the sleeve can detach and float down the intestine. The migrated sleeves can block the intestinal tract and may require surgery to remove. The device is meant to be removed after several months. However, removing the device is quite difficult as the metal barbs anchoring the device to the duodenum must be forcefully pulled out, which can increase the risk of complications, such as bleeding and perforation of the bowel.

Enrollments in the clinical study for the device were ended due to four cases of 325 implants resulting in hepatic abscesses. The anchoring system of the device has barbs that dig into the duodenum and may have caused infection and affected the liver. The hepatic abscess risk is likely related to the wire-induced ulceration within the duodenal bulb with either or both secondary bacterial seeding and perforation, either overt or microscopic. The construction of the anchoring mechanism is invasive, similar to the design of barbed wire, with a fixed diameter ring of barbed wire expanded within the proximal duodenal bulb. During the dwell time of the device (up to 12 months) there is localized tissue interaction by the direct expansion of the barbed ring and the contractile activity of the bulb, including superimposed MMC expulsive sweep contractions, creating potential risk issues for not only infection, but symptomatic ulceration and gross clinical perforation secondary to ulceration.

Another device, meant to improve on the anchoring technique of the above device, utilizes a stent straddling the pyloric sphincter to anchor the sleeve into the stomach. This avoids the complications associated with barbed elements described previously. This device includes a coupling mechanism to release the sleeve which provides the therapy.

This would allow the removal of the therapeutic sleeve, but not of the stent locking mechanism. The device may also be susceptible to migration.

A different type of device that has been developed in an attempt to cure obesity is implanted intragastric balloons (IGB), designed to fill space in the stomach. One such IGB has been implanted over 200,000 times internationally. A study has been completed that demonstrates that the balloon causes effective weight loss over the 9 months requested by the FDA, as measured either by % EWL (excess weight loss) or TBW (total body weight). The data also demonstrates a "legacy effect" which extends beyond 12 months during which patients continue to maintain weight loss after removal of the balloon at 6 months. A recent meta-analysis was performed on published experiences involving approximately 8,500 IGB patients showed that the device supports effective weight loss during 6 month use and a good safety profile. IGB cycling extended over long periods of time (years) in morbidly obese patients has also demonstrated weight loss which rivals that achieved by gastric bypass surgery. One IGB device is a silicone polymer device with performance characteristics at the present time which dictate safe use (low risk for collapse) during a 6 month dwell time. Another device is a dual IGB system made of a polymer with different response characteristics to gastric secretions over time. This balloon offers similar, but not better, weight loss results over 6 month use. Removal of this device is more complex than the single IGB and may ultimately be a deterrent over the use of a single balloon IGB, given similar weight loss outcomes. Both balloons induce weight loss by reducing capacity, inducing satiety, and delaying gastric emptying (only during the dwell period). There have been no formal studies documenting the physiology and mechanics of tolerance to an indwelling IGB with subsequent weight gain. It is speculated that this is due primarily to gastric distention and tolerance of greater volume.

Results from two randomized clinical trials of another IGB device were mixed. In one study with 43 patients, there was no difference between the twenty balloon patients and the twenty three receiving a placebo. In the second study with thirty two patients, the balloon patients had significantly greater decreases in BMI.

In addition to potentially unacceptable weight loss results, if a single balloon ruptures, the deflated balloon may migrate into the intestines and require surgical treatment. A dual balloon system is more robust by adding a second redundant balloon. If one balloon deflates, the second will continue to block migration until the device is removed. However, this dual balloon system is harder to fill and remove than the single balloon system. Patients may overcome the benefits of the space taken up by the balloon by continuing to overeat. This will distend the stomach and potentially obviate the advantage of the implant.

The disclosed gastrointestinal device addresses one or more of the disadvantages of the above devices by providing a safe, easily removable device with improved weight loss performance. The disclosed device may provide two mechanisms of weight loss, including a reduction in absorption gastric contents in duodenum and proximal jejunum and the slowing of gastric emptying to prolong/increase satiety. The device may also treat type 2 diabetes in both obese and non-obese patients. The device may be easily and safely deployed, either endoscopically or radiologically. A device which can be implanted by multiple physician specialties (e.g., endoscopically or radiologically) may broaden the potential base of users who can implant the device using either technique. When the desired amount of weight loss has been achieved, the device may be easily and atraumatically removed.

With reference to FIGS. 1-11, a device 10 is shown. The device 10 will be described herein as a gastrointestinal device 10, however, the device 10 may be used for any application in which a reduction in flow is desired between two regions of the body. As shown in FIG. 1, when used as a gastrointestinal device, the device 10 may be configured to straddle the pylorus 101 or pyloric sphincter 102, which connects the stomach 103 to the duodenum 104 (the first portion of the small intestine).

The device 10 may include a stent 12 and a connector assembly 14. The stent 12 may include a plurality of strands or wires 16. The strands 16 may be formed of any suitable material, such as a metal or polymer. In at least one embodiment, the strands 16 are formed of a shape-memory or heat-formable material. The strands 16 may also be formed of a highly elastic material, for example, a material that exhibits superelasticity. In one embodiment, the strands 16 may be formed from a nickel-titanium alloy, also known as nitinol. The strands 16 may be woven or braided together or they may be un-woven, separate strands 16.

In at least one embodiment, the strands 16 of the stent 12 may be formed into a first or proximal portion 18 and a second or distal portion 20. The first and second portions may have an enlarged diameter relative to the rest of the stent 12. The first portion 18 may be configured to be located proximal to the pylorus 101 within the stomach and the enlarged diameter may be configured to be larger than a maximum diameter of the pylorus to prevent distal movement of the stent 12. The second portion 20 may be configured to be located distal to the pylorus 101 within the duodenum and the enlarged diameter may be configured to be larger than a maximum diameter of the pylorus to prevent proximal movement of the stent 12. Together, therefore, the first and second portions may straddle the pylorus 101 and prevent the device from migrating proximally or distally past the pylorus.

The first and second portions may be disc or pancake shaped, such that they taper from a reduced diameter 22 to a maximum diameter 24 and back to a reduced diameter 22. The first and second portions may each define proximal and distal opposing surfaces 26 and 28. For example, the first portion 18 may form a proximal surface or face and an opposing distal surface or face, and the second portion 20 may form the same. Accordingly, the proximal surface 26 of the first portion 18 may face the stomach and the distal surface 28 of the first portion 18 may face the antral side of the pylorus, while the proximal surface 26 of the second portion 20 may face the distal side of the pylorus and the distal surface 28 of the first portion 18 may face the duodenal bulb.

The diameter of the first and second portions may continuously increase from one side to the maximum diameter 24 and then continuously decrease from the maximum to a reduced diameter 22 on the other side. The first or proximal portion 18 of the stent 12 may have a larger diameter (e.g., maximum diameter) than the second or distal portion of the stent 12. Since partially digested food (e.g., chyme) flows from the stomach into the small intestine, there will be a greater force or pressure on the device in the proximal to distal direction. Therefore, the first portion 18 may have a larger diameter in order to more effectively resist the pressure from the flow of partially digested food. In contrast, there are less forces or pressures acting in the distal to proximal direction on the second portion 20. For example, stomach churning (segmentation) occurs in the small intestine through muscular constriction of the intestinal wall. This process forces food backward and forward and may impose retrograde force on the device. Accordingly, the second portion 20 may have a smaller diameter since the risk of proximal migration is not as great. Furthermore, reducing the diameter of the second portion 20 relative to the first portion 18 may reduce the area of interaction between the device and the duodenum. This reduced diameter will reduce the risk for irritation of the duodenal tissue lining and avoid adverse effects such as ulceration and bleeding. The second portion 20 having a smaller diameter may also assist in insertion of the device by allowing it to pass through the pylorus more easily.

The first and second portions may both have a diameter (e.g., maximum diameter) that is larger than a diameter of the fully opened pylorus. In one embodiment, the first portion 18 may have a diameter, such as a maximum diameter, that is from 15 to 45 mm, or any sub-range therein. For example, the first portion 18 may have a diameter of 20 to 40 mm, 25 to 35 mm, or about 30 mm (e.g., ±5 mm). The first portion 18 may have a larger diameter than the second portion 20 (e.g., max diameters). In one embodiment, the second portion 20 may have a diameter, such as a maximum diameter, that is from 15 to 40 mm, or any sub-range therein. For example, the second portion 20 may have a diameter of 15 to 35 mm, 20 to 30 mm, or about 25 mm (e.g., ±5 mm). The difference between the first and second portion 20 diameters may be defined as a ratio. In one embodiment, a ratio of the diameter (e.g., max diameter) of the second diameter to the first diameter is less than 1:1. For example, the ratio may be less than 0.9:1, 0.8:1, 0.7:1, 0.6:1, or 0.5:1. In one embodiment, the ratio may be from 0.6:1 to 0.9:1. In another embodiment, the ratio may be from 0.7:1 to 0.9:1. In another embodiment, the ratio may be from 0.8:1 to 0.9:1. In another embodiment, the ratio may be from 0.75:1 to 0.85:1.

The plurality of strands 16 in the stent 12 may have a first, proximal end 30 and a second, distal end 32. The first and second ends of the stent 12 may be connected, attached, or otherwise coupled to the connector assembly 14. The connector assembly 14 may include two or more connectors or parts, including a proximal connector 34 and a distal connector 36. The proximal connector 34 may be spaced apart and configured to receive, couple, or attach to the first end 30 of the plurality of strands 16. The first end 30 of the strands 16 may extend in a proximal or antegrade direction from the first portion 18 of the stent 12 to couple to the proximal connector 34. The proximal connector 34 may therefore be proximal to the first portion 18 of the stent 12 when the device is in the deployed position and may reside in the stomach of the patient. The distal connector 36 may be configured to receive, couple, or attach to the second end 32 of the plurality of strands 16. The second end 32 of the strands 16 may extend in a distal or retrograde direction from the second portion 20 of the stent 12 to couple to the distal connector 36. The distal connector 36 may therefore be distal to the second portion 20 of the stent 12 when the device is in the deployed position and may reside in the duodenum of the patient.

The proximal and distal connectors may each have a plurality of openings or apertures 38 defined therein. The openings 38 may be spaced around a perimeter of the connectors in a generally annular pattern. The openings 38 may be configured to receive the strands 16 of the stent 12 and secure the strands 16 to the connector. For example, the openings 38 in the proximal connector 34 may receive and secure the first end 30 of the strands 16 and the distal connector 36 may receive and secure the second end 32 of the strands 16. The number of openings 38 in each connector may match or correspond to the number of strands 16 in the stent 12, although this is not required (e.g., there may be more or less openings). The strands 16 may be secured within the openings 38 in any suitable manner. For example, an adhesive may be applied to secure the strands 16, the strands 16 may be crimped or otherwise mechanically fastened within the openings 38, or the strands 16 may be welded (e.g., conventionally or ultrasonically) within the openings.

The connectors may have a generally circular cross section transverse to their longitudinal axes. The proximal and distal connectors may each have central channel or lumen 40 defined therein, which may be configured to allow chyme to flow through the device, as well as facilitate insertion and/or removal of the device. The proximal and distal connectors may each have a width or diameter that is less than the maximum diameters of the first and second portions of the stent 12. Accordingly, the stent 12 may have a reduced diameter portion 22 in the region where the first and second ends of the strands 16 attach to the proximal and distal connectors. In one embodiment, the stent 12 diameter may be at its minimum in the region where it attaches to the proximal and/or distal connector. The diameter of the stent 12 in the region where it attaches to the proximal and/or distal connector may be the same or similar to the diameter of the stent 12 in a region between the first and second portions. This region may be referred to as the valley between the first and second portions and may be the portion that is located within the pylorus when the device is deployed.

The connector assembly 14 may also include a middle connector 42 or middle portion 42. The middle connector 42 may extend at least partially between the proximal and distal connectors. In one embodiment, the middle connector 42 is not connected or attached to the stent 12. In the deployed configuration, the middle connector 42 may be located completely within the strands 16 of the stent 12 or surrounded by the strands 16. The middle connector 42 may be coupled at its proximal end to the proximal connector 34. The middle and proximal connectors may be coupled in any suitable manner. In one embodiment, the middle and proximal connectors are coupled via a threaded engagement 44. As shown in FIGS. 2, 3, 8, 10, and 11, the middle connector 42 may include male threads 46 that are configured to engage female threads 48 defined in the proximal connector 34. However, the threading may also be reversed, such that the middle connector 42 includes female threads and the proximal connector 34 includes male threads.

In at least one embodiment, the threaded engagement between the middle and proximal connectors is relatively coarse, or has a large pitch (e.g., fewer threads per axial distance). The threaded engagement may be a single start thread or a multiple start thread (e.g., two start or three start). In one embodiment, the male threads (e.g., on the middle connector 42) may have a pitch of 2 to 8 mm, or any sub-range therein. For example, the pitch may be from 3 to 7 mm, 3.5 to 6 mm, or about 4.2 mm (e.g., ±0.5 mm). The thread may have any suitable diameter, such as 0.25 to 0.5 inches or about 0.375 inches (e.g., ±0.1 inch). A large pitch, and therefore a large angle of repose, may allow the middle and proximal connectors to disengage or decouple more easily than a small pitch. The angle of repose may also be referred to as the angle of friction, and generally refers to the maximum angle at which a load can rest motionless on an inclined plane due to friction, without sliding down. In one embodiment, the angle of repose of the threaded engagement may be from 3 to 15 degrees, or any sub-range therein, such as 4 to 12 degrees, 5 to 10 degrees, or about 8 degrees (e.g., ±2 degrees). Additional properties that may affect the disengagement of the threads may include the lubricity and the smoothness of the connectors. In one embodiment, all of the connectors in the connector assembly 14 may be formed of a plastic, such as ABS, nylon, acetyl, Teflon, PP, or PE. Plastics generally have a high lubricity with each other and may allow the threads to disengage. In another embodiment, one or more of the connectors may be formed of metal, such as stainless steel. For example, the middle connector 42 may be partially or fully formed of a metal and the proximal and distal connectors may be formed of plastic. Metals and plastics generally have a high lubricity with each other and may allow the threads to disengage.

In order to prevent relative movement or unthreading between the middle and proximal connectors when the device is deployed, a release mechanism 50 may be provided to control the disengagement of the connectors. The release mechanism 50 may be configured to prevent relative movement of the connectors until the release mechanism 50 is activated or actuated. The release mechanism 50 may be any device capable of switching between a locked or unactuated position, in which the threads and prevented from disengaging, and an unlocked or actuated position, in which the threads are free to disengage. In one embodiment, the release mechanism 50 may include a pin or rod 52. The proximal and middle connectors may each include a groove or channel 54 that extends through their threads. When the connectors are threadedly engaged, the channels 54 may cooperate to form a passage 56 that is configured and sized to receive the pin 52. Accordingly, when the pin 52 is inserted into the passage 56, the threads of the proximal and middle connectors are locked together and cannot be unscrewed. When the pin 52 is not inserted in the passage 56, the threads are able to be unscrewed. The pitch of the threads may be configured to allow the proximal and middle connectors to be unscrewed with relatively little force being applied when the pin 52 is not inserted.

The middle connector 42 may include at least one projection 58 extending from its proximal end 60 toward its distal end 62. There may be two, three, four, or more projections, for example, 2 to 10, 2 to 8, 2 to 6, or 2 to 4 projections. The projections may be radially spaced to form a channel or passage 64 extending from the proximal connector 34 towards the distal connector 36. Each projection 58 may include a snap fit element or barb 66, which may be located at a distal tip 68 of the projection. The snap fit elements may include a stop 70 extending perpendicular or substantially perpendicular to the long-axis of the projection 58 and radially outward. The snap fit elements may also include a ramp 72 extending at an angle from the stop 70 to a tip of the projection. The projections 58 may be formed of a resilient material that can deform or deflect from its original position and return to its original position.

The snap fit elements of the middle connector 42 may be configured to engage a flange or lip 74 of the distal connector 36 when the device is in the deployed position. The flange or lip 74 may be annular or extend around a perimeter of the distal connector 36. The flange or lip 74 may also be continuous around the perimeter or may have gaps or interruptions. The stops 70 of the snap fit elements may engage the flange or lip 74 when the device is in the deployed position and prevent the distal and middle connectors from being pulled away from each other. Accordingly, when the device is in the deployed position, the proximal, middle, and distal connectors may be coupled together such that the proximal and distal connectors cannot move axially apart or away from each other. The proximal and middle connectors may be coupled by a threaded engagement and the middle and distal connectors may be coupled by snap fit elements of the middle connector 42 engaged with a flange on the distal connector 36.

The distal connector 36 may include a threaded portion 76 to facilitate insertion, movement, or alteration of the device. The threaded portion 76 may include male or female threading. The threaded portion 76 may be integral to the distal connector 36 or it may be a separate component that is attached or coupled to the distal connector 36 (e.g., by adhesive or welding). The channel or lumen of distal connector 36 may extend through the threaded portion 76 such that partially digested food passes through the threaded portion 76 when the device is deployed.

The device may further include a sleeve 78 configured to extend into the duodenum and, in some embodiments, into the proximal jejunum. The sleeve 78 may be formed of a biocompatible polymer and may be impermeable or semipermeable with respect to partially digested food and stomach fluids that are passed from the stomach to the small intestine. The sleeve 78 may be hollow, such that a lumen or passage is formed from a proximal end of the sleeve connected to the device to a distal end of the sleeve. The proximal end 80 of the sleeve may be attached to the distal connector 36. The attachment may be rigid or fixed, such that removal of the device requires removal of the sleeve, and vice versa. For example, the sleeve may attached by adhesive (e.g., glue) or welded to the distal connector 36. The sleeve may connect to the distal connector 36 such that it surrounds an exit of the lumen in the distal connector 36. The sleeve may be dip or blow molded from one of several polymers, such as PTFE (Teflon), polyurethane or silicone.

Accordingly, partially digested food may travel from the stomach, through the lumens of the proximal connector 34 and the distal connector 36, through the sleeve, and exit in a distal portion of the duodenum or in the jejunum. The sleeve therefore is configured to reduce or eliminate the absorption of nutrients in the duodenum and proximal jejunum (depending on sleeve length), thereby reducing the number of calories absorbed by the patient.

Since the device may be deployed over a relatively long time period, it may be important to minimize or prevent tissue in-growth into the stent 12. Tissue in-growth may inhibit removal of the device and may cause removal to be traumatic to the tissue in and around the pylorus. In at least one embodiment, the spaces between the strands 16 in the stent 12 may be blocked or filled to prevent tissue in-growth. In one embodiment, the stent 12 may be partially or completely surrounded by a sheath 82. The sheath 82 may be formed of a polymeric material, such as an elastomer (e.g., silicone). The sheath 82 may surround at least the first and second portions of the stent 12, and may cover all externally exposed strands 16. By covering the strands 16 of the stent 12, tissue in-growth may be prevented and the device may remain detached from the stomach, pylorus, and duodenum of the patient. The sheath 82 may be flexible and elastic enough that it conforms to the outer shape of the stent 12 in both the deployed and collapsed configurations (explained in more detail below).

In another embodiment, the strands 16 of the stent 12 may be partially or completely embedded within a polymeric material, such as an elastomer (e.g., silicone). In this embodiment, the strands 16 are not covered on one side or surface, but encapsulated by the polymeric material such that the strands 16 are not exposed to the environment/surroundings at all. Embedding the strands 16, or at least a portion of the strands 16, in a polymeric material may minimize or prevent tissue in-growth, as described above, as well as provide additional resistance to corrosion. While an outer sheath may protect the strands 16 from exterior corrosive substances, the strands 16 may still be exposed on an interior of the stent 12. Embedded strands 16 may be isolated from corrosive substances, such as stomach acids, both external and internal to the stent 12. In one embodiment, the strands 16 may be embedded in the polymeric material (e.g., silicone) by inflating a balloon inside the stent 12 and dipping the stent 12 in liquid silicone. However, any suitable method of embedding the strands 16 in the polymeric material may be used. The polymeric material may be flexible and elastic enough that it conforms to the shape of the stent 12 in both the deployed and collapsed configurations (explained in more detail below).

When the device is deployed across the pylorus of a patient, a lumen or channel 84 may be formed from the stomach, through the proximal, middle, and distal connectors (the connector assembly 14), and into the sleeve (or into the duodenum if there is no sleeve). Partially digested food (e.g., chyme) may therefore travel through the lumen 84 in the device in a manner similar to the pylorus (e.g., without the device). It has been discovered, however, that reducing the flow of chyme from the stomach into the intestines, and thereby slowing the rate of gastric (stomach) emptying, may result in weight loss in a patient. By increasing the time for the stomach to empty, the patient feels full, or satiated, for longer. This prolonged feeling of fullness reduced the desire to eat, which may result in less calories being consumed.

In at least one embodiment, the lumen 84 of the connector assembly 14 may be sized and configured to reduce the flow of partially digested food from the stomach to the small intestine. The lumen 84 may have a diameter that is smaller than a diameter of the pylorus, thereby increasing the resistance to the flow of chyme and slowing gastric emptying. The lumen 84 may have a constant, or substantially constant, diameter or the diameter may vary along a length of the lumen 84. The diameter of the lumen 84 may be smaller than a diameter of the pylorus in at least one region of the lumen 84. For example, the lumen 84 may be smaller than a diameter of the pylorus within the proximal connector 34 channel, within the middle connector 42, and/or within the distal connector 36 channel. The lumen 84 may be narrower than the pylorus in more than one region and it may be as wide as the pylorus in some regions. In one embodiment, the lumen 84 may be narrowest within the distal connector 36 channel.

The more resistance to flow that is created, the slower the gastric emptying will be, and more weight loss should occur. Accordingly, the size of the lumen 84 may be designed or configured based on the level of obesity in the patient being treated. For morbidly obese patients, the lumen size may be made smaller than for a slightly or moderately obese person. Accordingly, the size of the lumen 84 and the aggressiveness of the weight loss goal can be tailored to each patient depending on their situation and needs. The typical pyloric diameter has been measured to be from about 7 to 10 mm. In one embodiment, at least a portion of the lumen 84 of the device may be from 3 to 7 mm, or any sub-range therein. For example, the lumen size may be 4 to 6 mm or about 5 mm (e.g., ±0.5 mm). The lumen size may be adjusted by changing the channel size of the proximal and/or distal connector 36.

The device may be deployed or inserted into the patient through the mouth and into the esophagus and stomach. Since the device is inserted through the mouth, the procedure may be performed using endoscopic or radiological guidance. The device may include radiological markers (not shown) to facilitate insertion using fluoroscopy. The procedure may also be an outpatient procedure, making it less expensive and less traumatic for the patient. Insertion and deployment of the device is shown in FIGS. 8-11. In order for the device to be inserted orally into the patient, it may be manipulated into an insertion or deployment configuration. The device may be placed in the insertion configuration with the middle connector 42 coupled to the proximal connector 34 but not to the distal connector 36 (e.g., the distal connector 36 is detached from the rest of the connector assembly 14 but remains attached to the strands 16 of the stent 12). While in this state, the distal and proximal connectors may be stretched or pulled axially away from each other to cause the strands 16 in the first and second portions to straighten. The distal and proximal connectors may be axially separated until the strands 16 in the stent 12 are parallel, or substantially parallel, to each other (e.g., aligned along the long axis of the device). Once in this insertion configuration, the device may be inserted into a protective sheath 86. The protective sheath 86 may restrict the device from returning to its natural or relaxed position (which may have been previously heat formed) prematurely. The sheath 86 may also protect the lining of the mouth, esophagus, and stomach during insertion of the device.

The device may be manipulated into the insertion configuration using any suitable manner. For example, the proximal and distal connectors may be pulled apart manually or using a fixture. In one embodiment, a torque catheter 88 and a balloon catheter 90 may be used to move the device into the insertion configuration. The torque catheter 88 may be a catheter having a high torque capability, such that it is able to apply torque at its end or tip. For example, the torque catheter 88 may include braiding of fabric or metal to increase its ability to apply torque before the catheter twists or distorts. The end or tip of the torque catheter 88 may have an engagement portion 92, such as a fastener, attached thereto. The engagement portion 92 may be integrally formed with the torque catheter 88 (e.g., as a single component), or it may be attached using adhesive, a fastener, or other known methods. In at least one embodiment, the engagement portion 92 may include a fastener having threading that is configured to engage the threaded portion 76 of the distal connector 36. The fastener may have male threading to engage with female threading in the threaded portion, or vice versa. While the fastener may engage the distal connector 36 using threading, other methods of releasable attachment may be used. The torque catheter 88 may also be referred to as a torque tube or a torque cable, and may have a lumen or passage extending therethrough. The torque tube may therefore be passed over the guide wire 94 and through the lumen in the proximal connector 34 and the lumen in the middle connector 42 to engage and releasably couple to the distal connector 36.

The balloon catheter 90 may also have a lumen or passage extending therethrough, and the lumen may be sized to be passed over both the guide wire 94 and the torque catheter 88. The balloon catheter 90 may be inserted with the balloon in a deflated state and inflated within the patient, as is known in the art. To move the device into the insertion configuration, the fastener of the torque tube 88 may be engaged and coupled to the distal connector 36, such as by engaging the threads of the threaded portion 76. The balloon catheter 90 may be inserted at least partially into the proximal connector 34, for example, at least partially into the lumen, in a deflated state and then inflated such that it is secured by friction within the proximal connector 34. To move the device to the insertion configuration, tension may be applied to the distal connector 36 by the torque tube 88 and the proximal connector 34 may be pulled axially away from the distal connector 36 using the balloon catheter 90. Once in the insertion configuration (e.g., strands 16 parallel in axial direction), the device may be inserted into the protective sheath.

In one embodiment, the device 10 (e.g., within a protective sheath) may be inserted over a guide wire 94, for example, a standard 0.035 inch or 0.038 inch guide wire. The guide wire 94 may be inserted into the mouth of the sedated patient, through the esophagus and stomach, and into the duodenum. The device, optionally enclosed in a protective sheath, may then be inserted into the patient over the guide wire 94 (e.g., by inserting the other end of the guide wire 94 through the lumen of the connector assembly 14). The device may be inserted with the torque tube 88 engaged with the distal connector 36, such as through a threaded engagement between the fastener and the threaded portion 76. The physician may use a contrast agent, such as barium sulfate solution, or direct endoscopy to locate the pylorus and pyloric sphincter. The physician may position the device within the pylorus while the device is in the insertion configuration and, optionally, within a protective sheath.

The device may be positioned such that when the device is in the deployed configuration, the first portion 18 is proximal to the pylorus and the second portion 20 is distal to the pylorus. When the device is positioned correctly, the protective sheath may be removed (if present). Removal of the sheath may allow the device to return to its natural or relaxed configuration having the first and second portions with enlarged diameters (e.g., "humps"). To lock or secure the device into the deployed configuration, the distal and proximal connectors may be moved or pulled axially towards each other. The device may be locked by pushing or applying a forward axial force (e.g. in a direction from the proximal connector 34 towards the distal connector 36) on the proximal connector 34 using the balloon catheter 90 while applying a pulling or applying a rearward axial force on the distal connector 36 using the torque tube 88. The forces applied may cause the proximal connector 34 to stay relatively stationary while the distal connector 36 moves towards the proximal connector 34 (e.g., force is applied to the balloon catheter 90 to hold the proximal connector 34 in place) or vice versa (e.g., force is applied to the torque tube 88 to hold the distal connector 36 in place and the balloon catheter 90 is pushed towards the distal connector 36). The forces may also be applied such that both the proximal and distal connectors move towards each other.

In the insertion configuration, the middle connector 42 may be coupled to the proximal connector 34, for example, by a threaded connection (described above). Accordingly, when the proximal and distal connectors move towards each other, the middle connector 42 may engage and couple to the distal connector 36 to lock the connector assembly 14 together. When the middle connector 42 is pulled toward the distal connector 36, the projections 58 of the middle connector 42 may engage the flange or lip 74 of the distal connector 36 and flex or deflect. The deflection may be facilitated by the ramp(s) on the snap fit element(s) 66 of the projection(s) 58, which may provide an angled surface that causes the projections to deflect inward towards a longitudinal axis or center line of the middle connector 42. As the middle connector 42 continues to move toward the distal connector 36, the ramp(s) of the snap fit elements 66 may extend beyond or passed the flange 74 of the distal connector 36 and the projections may flex or deflect back to their original position, or close thereto (e.g., the projections may still be flexed slightly inward). Once the snap fit elements 66 extend distally beyond the flange 74 of the distal connector 36, the stops of the snap fit elements may engage the flange and prevent the middle connector 42 from moving rearward or proximally from the distal connector 36 (or the distal connector 36 from moving forward or distal from the middle connector 42). The projections and snap fit elements may be sized such that the distal tips of the snap fit elements contact or nearly contact a portion of the distal connector 36 distal to the flange. This may prevent additional relative movement between the middle and distal connectors in the opposite direction (e.g., towards each other) once they are engaged and locked.

Engaging and locking the connector assembly 14 together may move the stent 12 from its relaxed position into the deployed configuration. Since the first and second ends of the strands 16 may be connected to the proximal and distal connectors, respectively, bringing the proximal and distal connectors together may move the strands 16 from a relatively gentle or mild hump into a more steep disc or "pancake" shape. The locked stent 12 may form the first and second portions, with the sizes and dimensions described above.

Once the device is locked into the deployed configuration, the balloon catheter 90 and the torque catheter 88 may be removed. The balloon catheter 90 may first be deflated. Then, the fastener of the torque catheter 88 may be decoupled from the distal connector 36, for example, by unscrewing from the threaded portion, and withdrawn over the guide wire 94. However, the order of removal may also be reversed (e.g., torque tube removed first, then balloon catheter 90).

During insertion, the duodenal (or duodenal-jejunal) sleeve may be in a compact, condensed, or rolled-up configuration. In one embodiment, the sleeve may be attached to the device (e.g., to the distal connector 36) which is enclosed in the protective sheath. The sleeve may be formed of a very thin walled polymer (e.g., less than 25 microns wall thickness) which may be inserted between the protective sheath and the device (e.g., the stent 12). The sheath may be rolled, folded, crumpled, or loose when inserted. To prevent the sheath from emerging from the protective sheath prematurely, the duodenal sleeve may include a loop of material, such as a suture, which restrains the duodenal sleeve. A release mechanism, such as a slip knot, in the material may allow the implanting physician to release the sheath by pulling on the release mechanism. When the protective sheath is ready for removal, the stent 12 may be across the pyloric sphincter and the sleeve may be downstream in the duodenum and proximal jejunum. The protective sheath covering the stent 12 and sleeve may be removed by pulling the protective sheath in a retrograde direction axially towards the mouth while applying a fixed force to the balloon catheter 90 and torque tube. The sleeve may be released into the duodenum and the stent 12 can be positioned to straddle the pyloric sphincter.

In another embodiment, the sleeve may be rolled up or folded. Similar to above, the rolled up sleeve may be deployed downstream into the duodenum and jejunum. In one embodiment, the sleeve may be deployed by applying fluid pressure to the sleeve. A balloon catheter 90 having an elastomeric seal (e.g., a Touhy-borst connector) may seal the guide wire 94 while allowing fluid such as saline or water to be pushed down the lumen of the catheter around the guide wire 94. Once the device is locked into the deployed configuration, the sleeve may be released and allowed to move or "float" into and down the duodenum and proximal jejunum (depending on length). The sleeve may be pushed down the duodenum by natural forces (e.g., without further action by the physician), such as the flow of partially digested food. Alternatively, the sleeve may be pushed or assisted down the duodenum by the physician. In one embodiment, a balloon catheter, which may be the same or different from the balloon catheter used to position and lock the device) may be inflated and extended over the guide wire 94 to push the sleeve into and down the duodenum (and proximal jejunum, depending on length). If the balloon catheter is the same one used for positioning and locking the device, it may be used to deploy the sleeve prior to being withdrawn or it may be re-inserted after being withdrawn.

The device may be removed after insertion in a simple out-patient procedure, similar to insertion. The device may be removed when the patient has lost a certain amount of weight, or for any other reason. As described above, when the device is in the deployed configuration, the connector assembly 14 may be locked such that the distal, middle, and proximal connectors cannot separate and the stent 12 maintains the first and second portions having enlarged diameters. In order to remove the device, the connector assembly 14 may be unlocked such that the stent 12 may be collapsed or condensed into a retrieval configuration. The retrieval configuration may be similar to the insertion configuration, in that the strands 16 of the stent 12 may be parallel or substantially parallel and aligned along the longitudinal axis of the device. To unlock the device, the proximal connector 34 may be decoupled from the middle connector 42 (which may be locked to the distal connector 36 by snap fit elements). Since the strands 16 of the stent 12 may be unattached to the middle connector 42, the middle connector 42 may be disconnected from either of the proximal or distal connectors in order to unlock the device.

In one embodiment, described above, the middle connector 42 and the proximal connector 34 may be coupled by a threaded engagement. In this embodiment, a release mechanism 50 may be provided to control the disengagement of the middle and proximal connectors. The release mechanism 50 may be configured to prevent relative movement of the connectors until the release mechanism 50 is activated or actuated. As described above, the release mechanism 50 may include a pin or rod 52, which may be inserted into a passage formed in the middle and proximal connectors. The pin 52 may prevent the threads of the proximal and middle connectors from unscrewing when the pin 52 is inserted. The pitch of the threads may be configured to allow the proximal and middle connectors to be unscrewed with relatively little force being applied when the pin 52 is not inserted.

The release mechanism 50 may also include a hook or curved/bent portion 96. The hook 96 may extend from the pin 52 and may be configured to be snared. The release mechanism 50 may be tethered or attached to the device, for example, to the proximal connector 34. The release mechanism 50 may be tethered at the pin, the hook 96, or another location. The attachment to the device may be flexible or rigid. In one embodiment, the tether 98 is a flexible polymer thread or a suture. The attachment of the tether to the release mechanism 50 and/or device may be by adhesive, welding (e.g., ultrasonic), by mechanical fastening, knotting, or any other suitable method. In one embodiment, the hook 96 may be formed from tubing (e.g., hypodermic tubing) and the hooked tubing may be swaged the around a high strength chord material. For example, Kevlar twine may be used as a tether and may be swaged to the hook. The tether may be attached to the proximal connector 34 by tying the tether 98 directly to the connector. The proximal connector 34 may include several holes 100 (e.g., molded in) through which the tether is threaded and tied.

To unlock the connector assembly 14, a snare (not shown) may be inserted into the mouth and through the esophagus and stomach. The snare may be any device configured to engage and actuate the release mechanism 50. If the release mechanism 50 includes a hook 96, the snare may include a loop or a hook to engage the hook 96. The snare may be inserted by itself or through/over a catheter or guide wire 94 or within a sleeve/sheath. A physician may use an endoscope or radiology (e.g., fluoroscopy), or any other suitable approach, to guide the snare.

When the device is to be removed, the physician may use the snare to engage and actuate the release mechanism 50. This may include looping a snare over a hook 96 of the release mechanism 50 and pulling on the hook 96 to remove the pin 52 from the passage 56 (or at least remove it from blocking the threads of the connectors). Once the pin 52 is removed, the threads of the middle and proximal connectors may no longer be locked and prevented from unscrewing. As described above, the threads may be configured to unscrew relatively easily (e.g., large pitch and angle of repose). To facilitate the unscrewing of the threads, the physician may continue pulling on the hook 96, which may be tethered to the proximal connector 34. The axial pulling force may cause the threads to unscrew, thereby uncoupling the middle and proximal connectors. Since the stent 12 may only be attached to the distal and proximal connectors, continued pulling on the hook 96 using the snare may cause the strands 16 of the stent 12 to straighten out. The stent 12 may be pulled until the strands 16 are parallel or substantially parallel to each other, which may be referred to as the retrieval configuration. The retrieval configuration may be similar to the insertion configuration, except that the proximal connector 34 is free and the middle and distal connectors are coupled in the retrieval configuration.

The stent 12 may be pulled into a protective sheath (e.g., similar to the sheath used for insertion) by pulling on the snare and hook 96 until the stent 12 is fully collapsed inside the protective sheath. Once the stent 12 is pulled into the retrieval configuration within the protective sheath, the device and sheath may be removed through the patient's mouth, for example, by continued pulling on the release mechanism 50 using the snare (e.g., a loop over a tethered hook 96) or by pulling on the sheath. Since the duodenal sheath may be fixed to the device, it may also be removed through the mouth. The protective sheath may prevent trauma to the stomach, esophagus, and mouth during removal.

Alternatively, the device may be removed without the protective sheath. In this embodiment, a counter axial force may be applied to the device to stretch the strands 16 and cause the strands 16 to straighten into the retrieval configuration. To remove the device without a protective sheath, a guide wire 94 may be threaded through unlocked stent 12 to allow a torque catheter 88 to travel over the wire and engage with the distal connector 36. Once the torque tube with the threaded distal end engages the female threads on the distal connector 36, the torque tube can be screwed to the distal connector 36. A balloon catheter 90 may be slid over the torque tube/guidewire and the balloon may be inflated to frictionally engage the proximal connector 34. By pushing on the torque tube while axially pulling the balloon catheter 90, the stent 12 can be stretched such that the strands 16 straighten. The stretched stent 12 can be removed by pulling both the torque tube and balloon catheter 90 from the patient's mouth. The attached duodenal sleeve will follow the stent 12 and emerge through the patient's esophagus and mouth.

The disclosed device and methods allow for a simple procedure performed through a natural orifice (mouth) without any incisions or stapling. As a result, the device may dramatically reduce the complication rate compared to other approaches. Such an effective non-surgical alternative weight loss procedure may significantly decrease the rising burden of health care costs in the US and around the globe. The procedure is reversible, technically easy, does not require hospitalization, is cost effective relative to surgery, and produces effective long term weight loss. The device may inhibit weight loss and reduce type 2 diabetes. The device may be used to treat patients who are not morbidly obese so that the treatment of type 2 diabetes can be introduced earlier in the progression of the disease, since researchers have shown that treating less advanced cases of diabetes via surgical techniques have much lower likelihood to re-develop the disease. The device may provide a dual solution for weight loss; a restricted pyloric canal to slow food passage and a duodenal-jejunal sleeve to prevent absorption of nutrients in the small intestines. The device uses a benign anchor locking and unlocking system which does not rely on barbs or hooks to retain the stent nor the duodenal sleeve in place. The stent may be encapsulated in a sheath to prevent tissue in growth and ease removal. The device can be easily implanted and explanted by physicians from multiple specialties through the natural orifice of the mouth.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A gastrointestinal device for reducing flow through a pyloric sphincter of a patient, the device comprising:
    a stent including a plurality of strands forming first ends and second ends, the plurality of strands configured to form a proximal portion having a proximal diameter and a distal portion having a distal diameter, wherein the proximal and distal diameters are larger than a diameter of the pyloric sphincter, and the proximal diameter is larger than the distal diameter; and
    a connector assembly, comprising:
        a proximal connector;
        a distal connector, wherein the plurality of strands are attached at the first ends to the proximal connector and at the second ends to the distal connector; and
        a middle portion extending between the proximal connector and the distal connector within the plurality of strands, wherein the middle portion comprises a threaded portion configured to engage a corresponding threaded portion of the proximal connector.

2. The device of claim 1, wherein a ratio of the distal diameter to the proximal diameter is from 0.6:1 to 0.9:1.

3. The device of claim 1, wherein the proximal portion of the stent is configured to prevent distal movement of the device through the pyloric sphincter, and the distal portion of the stent is configured to prevent proximal movement of the device through the pyloric sphincter.

4. The device of claim 1, wherein the connector assembly defines a lumen having a diameter that is less than the diameter of the pyloric sphincter and configured to reduce a flow of partially digested food through the pyloric sphincter.

5. The device of claim 1, further comprising a sleeve fixed to the distal connector and configured to extend into a duodenum of the patient, the sleeve configured to receive partially digested food from the connector assembly.

6. The device of claim 1, wherein the middle portion further comprises at least one projection extending towards the distal connector, the at least one projection including a snap fit element configured to engage a flange on the distal connector and prevent proximal movement of the middle portion relative to the distal connector.

7. The device of claim 1, wherein the plurality of strands extend in a proximal direction from the proximal portion to attach to the proximal connector at the first end and extend in a distal direction from the distal portion to attach to the distal connector at the second end.

8. The device of claim 1, wherein the proximal portion and the distal portion are configured to straddle the pyloric sphincter, and wherein the proximal portion and the distal portion each define proximal and distal opposing surfaces.

9. The device of claim 1, wherein the proximal portion and the distal portion are configured to straddle the pyloric sphincter and the proximal diameter tapers to a reduced diameter adjacent to the proximal connector and the distal diameter tapers to a reduced diameter adjacent the distal connector.

10. The device of claim 1, wherein the plurality of strands is embedded within an elastomer.

11. The device of claim 1, wherein the plurality of strands is embedded within silicone.

12. A gastrointestinal device for reducing flow through a pyloric sphincter of a patient, the device comprising:
    a stent including a plurality of strands forming first ends and second ends, the plurality of strands configured to form a proximal portion having a proximal diameter and a distal portion having a distal diameter, wherein the proximal and distal diameters are larger than a diameter of the pyloric sphincter; and
    a connector assembly, comprising:
        a proximal connector;
        a distal connector; and
        a middle portion extending between the proximal connector and the distal connector, wherein the middle portion comprises:
            a threaded portion configured to engage a corresponding threaded portion of the proximal connector; and
            at least one projection extending towards the distal connector, the at least one projection including a snap fit element configured to engage a flange on the distal connector and prevent proximal movement of the middle portion relative to the distal connector,
    wherein the plurality of strands is attached at the first ends to the proximal connector and at the second ends to the distal connector, and
    wherein the connector assembly middle portion extends within the plurality of strands.

13. The device of claim 12, wherein a ratio of the distal diameter to the proximal diameter is from 0.6:1 to 0.9:1.

14. The device of claim 12, wherein the plurality of strands is embedded within silicone.

15. A gastrointestinal device for reducing flow through a pyloric sphincter of a patient, comprising:
   a stent including a plurality of strands forming first and second ends, the plurality of strands configured to form a proximal portion having a proximal diameter and a distal portion having a distal diameter, wherein the proximal and distal diameters are larger than a diameter of the pyloric sphincter; and
   a connector assembly including a proximal connector, a distal connector, and a middle portion extending there between, the plurality of strands being attached at the first end to the proximal connector and at the second end to the distal connector, and the connector assembly middle portion being unattached to the plurality of strands.

16. The device of claim 15, wherein a ratio of the distal diameter to the proximal diameter is from 0.6:1 to 0.9:1.

17. The device of claim 15, wherein the middle portion includes a threaded portion that is configured to engage a threaded portion of the proximal connector and the middle portion includes at least one projection extending towards the distal connector, the at least one projection including a snap fit element configured to engage a flange on the distal connector and prevent proximal movement of the middle portion relative to the distal connector.

18. A gastrointestinal device for reducing flow through a pyloric sphincter of a patient, the device comprising:
   a stent including a plurality of strands forming first ends and second ends, the plurality of strands configured to form a proximal portion having a proximal diameter and a distal portion having a distal diameter, wherein the proximal and distal diameters are larger than a diameter of the pyloric sphincter, and the proximal diameter is larger than the distal diameter; and
   a connector assembly, comprising:
      a proximal connector;
      a distal connector, wherein the plurality of strands are attached at the first ends to the proximal connector and at the second ends to the distal connector; and
      a middle portion extending between the proximal connector and the distal connector within the plurality of strands, wherein the middle portion comprises at least one projection extending towards the distal connector, the at least one projection including a snap fit element configured to engage a flange on the distal connector and prevent proximal movement of the middle portion relative to the distal connector.

19. The device of claim 18, wherein the middle portion further comprises a threaded portion configured to engage a corresponding threaded portion of the proximal connector.

* * * * *